Figure 1:
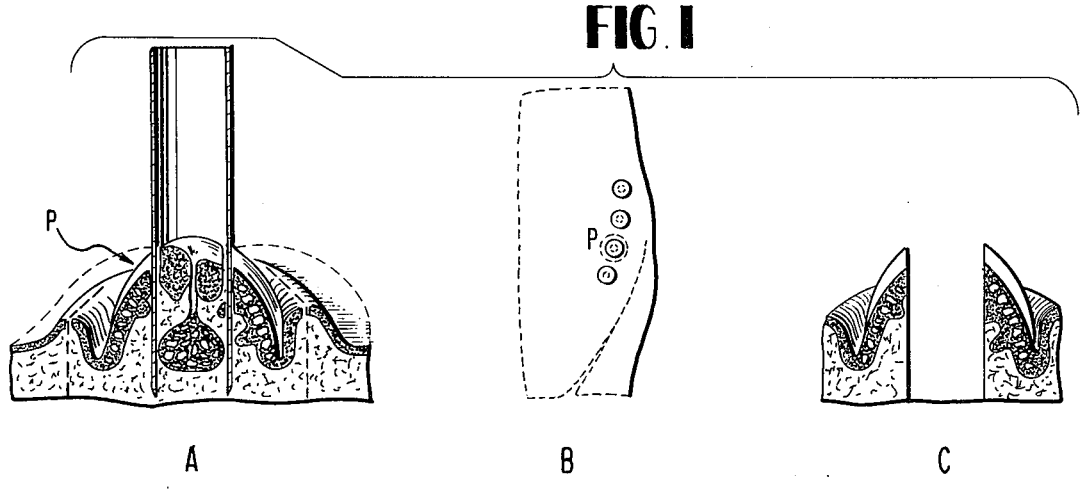

United States Patent [19]

Henkin

[11] 4,146,501

[45] Mar. 27, 1979

[54] PROCESS FOR ISOLATING AND PURIFYING TASTE BUD RECEPTORS FOR SCREENING AND EVALUATING TASTANTS

[76] Inventor: Robert I. Henkin, 6930 Selkirk Dr., Bethesda, Md. 20034

[21] Appl. No.: 753,984

[22] Filed: Dec. 27, 1976

Related U.S. Application Data

[63] Continuation of Ser. No. 640,340, Dec. 12, 1975, abandoned.

[51] Int. Cl.² .......................... C09K 3/00; G01N 1/00; G01N 31/14; G01N 33/16
[52] U.S. Cl. ................................ 252/408; 23/230 B; 195/1.7; 195/103.5 R; 424/1; 424/10; 424/95; 424/104
[58] Field of Search .................... 424/95, 10, 104, 1; 252/408; 195/103.5 R, 1.7; 23/230 B

[56] References Cited

PUBLICATIONS

Lum, Clark., K. L. et al., Fed. Proc., Vol. 32, No. 3, 328 Abs., 634 (Mar. 1973).
Lo, Chai-Ho; Biochim. Biophys. Acta, vol. 291, pp. 650-661 (1973).
Cagan, R. H., Biochim, Biophys. Acta., vol. 252, pp. 199-206 (1971).
Touster, O., et al., J. Cell. Biol., vol. 47, pp. 604-618 (1970).
Lum, Clark K. L., et al., Biochim. Biophys. Acta, vol. 421, pp. 353-361, pp. 362-379, pp. 380-394 (Feb. 1976).

*Primary Examiner*—Benjamin R. Padgett
*Assistant Examiner*—Gron, T. S.
*Attorney, Agent, or Firm*—LeBlanc & Shur

[57] ABSTRACT

A process for isolating and purifying taste bud receptor material for screening and evaluating tastants is described. The process includes surgically excising a plurality of circumvallate papillae, coring said papillae to remove the central mucous gland from each, followed by exposing the taste bud bearing epithelial portion thereof. The buds are preferably exposed by swelling in a hypotonic medium followed by subjecting said buds to about 900 psi in a nitrogen bomb. The swelled buds are then subjected to a gentle, selective homogenization to extrude taste bud receptor material therefrom without substantial destruction of surrounding epithelial tissue. The extruded material is then isolated by filtering and purified by subjecting the filtrate to differential centrifugation to isolate a receptor containing membrane enriched fraction. The fraction is then further purified by sucrose gradient centrifugation to isolate a receptor containing membrane enriched subfraction substantially without contaminating materials capable of binding tastants. The subfraction is then utilized as a medium for evaluating tastants wherein radioactive labeled tastant compounds are incubated with said subfraction until equilibrium is reached, and the quantity of labeled tastant is bound to the receptor material may then be measured. Unlabeled tastants may also be incubated with said labeled tastant bound medium to evaluate the strength of the binding, and other related taste characteristics.

11 Claims, 11 Drawing Figures

A  B  C

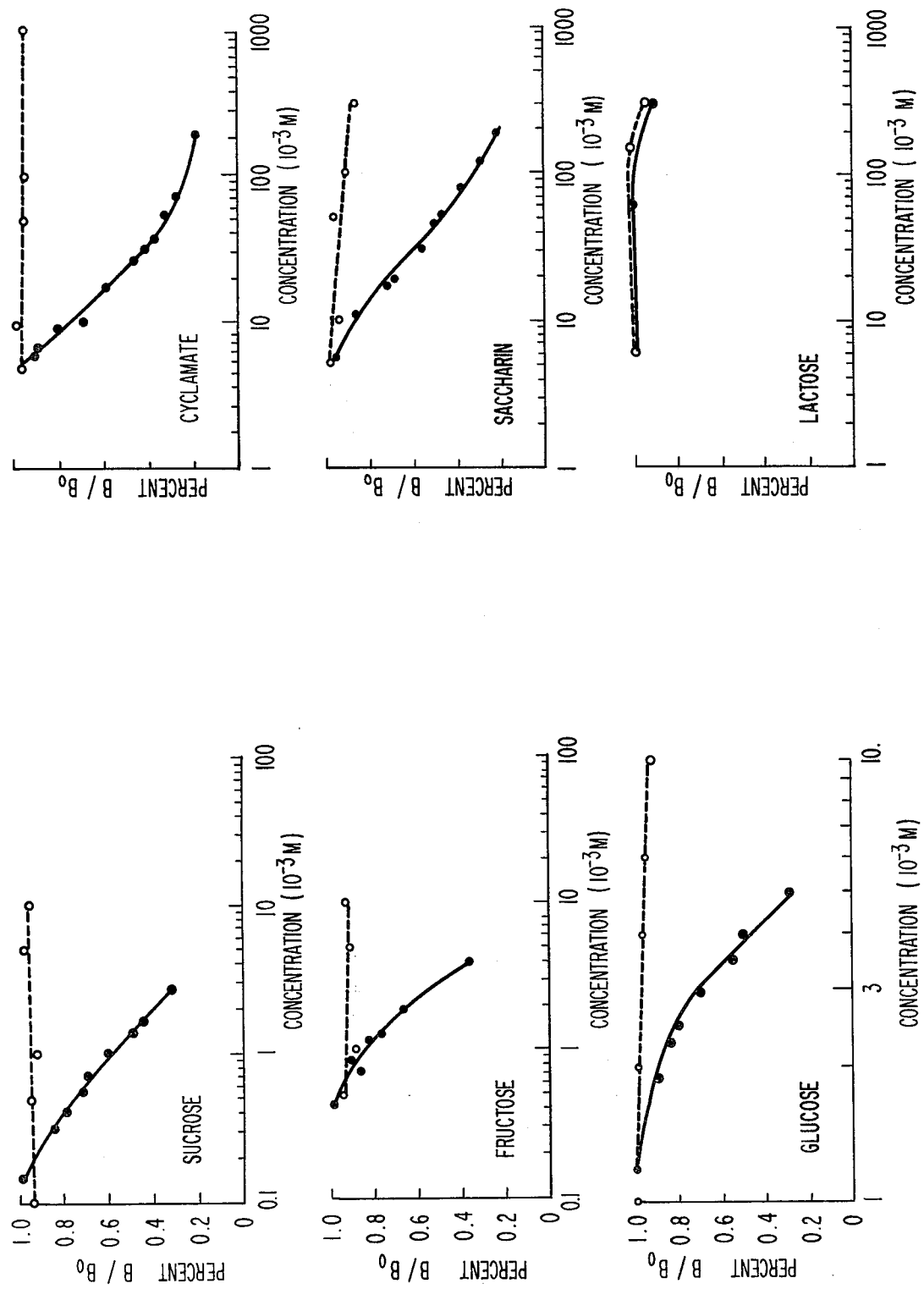

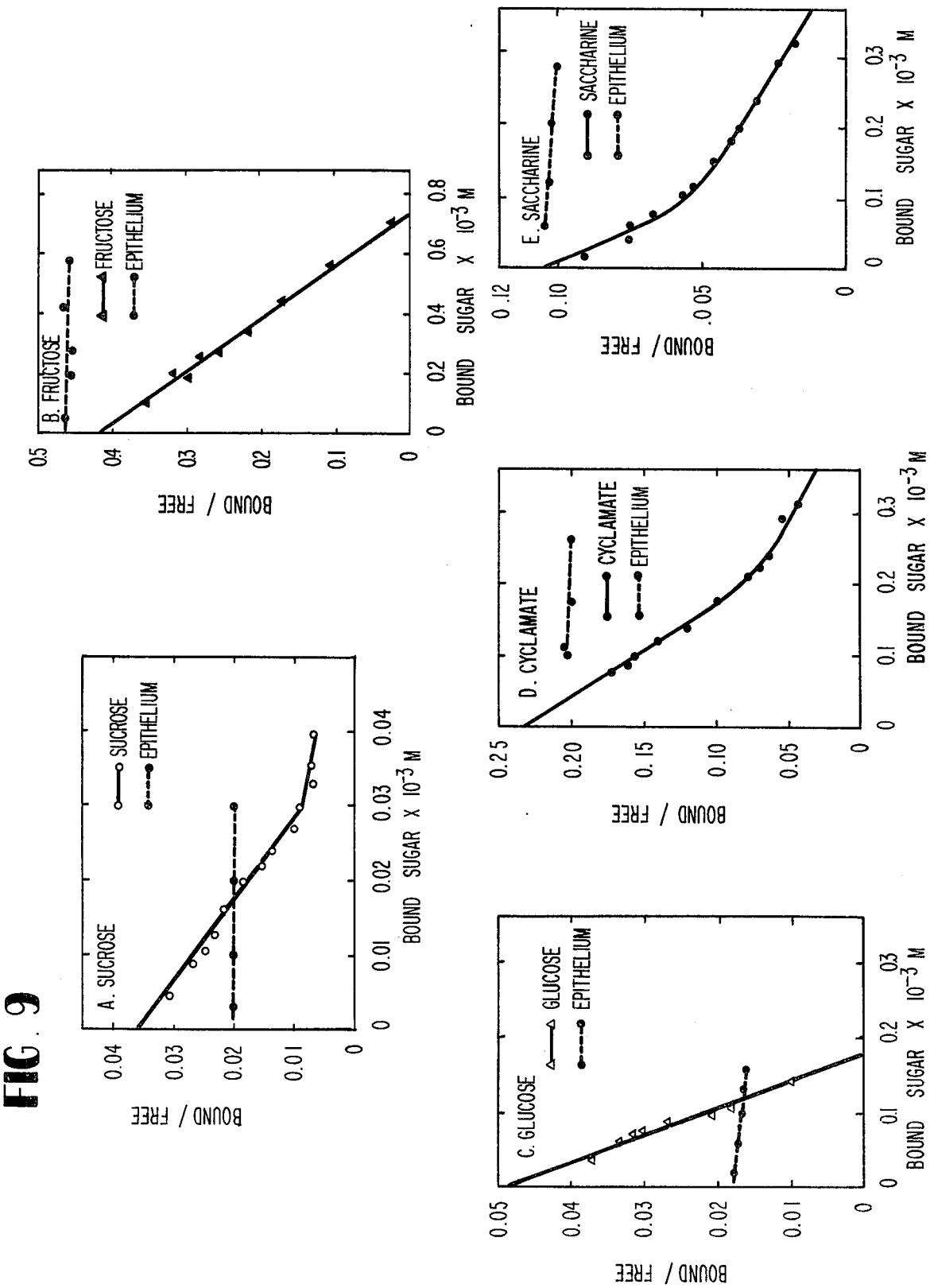

PROCESS FOR ISOLATING AND PURIFYING TASTE BUD RECEPTORS FOR SCREENING AND EVALUATING TASTANTS

This is a continuation of application Ser. No. 640,340 filed Dec. 12, 1975, now abandoned.

While the word "tastant" used hereinafter has been generally understood to include substances having taste quality, it will be obvious to those skilled in the art that the process of this invention is equally applicable to evaluating (1) substances largely without taste which act by binding to taste bud membranes; and (2) other substances which are involved in taste bud function whose action depends upon binding to the receptors of the taste bud membrane.

The initial or preneural event of taste has been postulated as the adsorption of a taste stimulus to the taste receptor and experimental evidence supports the concept that a weak tastant-receptor complex is formed at the apical surface of the taste bud. To establish these events, investigators have attempted to bind unlabeled sugars, bitter substances, and radioactively labeled sugars to taste bud material. However, either the homogenates of the entire lingual epithelium or the homogenates of whole taste bud bearing papillae used in these studies limited their specificity and produced inconsistent results. It was also difficult to impossible to interpret these results because the test preparations used included many substances other than taste bud material which could readily bind sugars or alkaloids in addition to the very small fraction obtained from taste buds. The lack of adequate controls further limited the results of these studies.

In order to obtain a more specific tissue for binding studies, the more apical portions of taste buds of, for example, bovine origin, were isolated according to this invention with only minimal contamination from other structures, and purified to obtain membrane enriched subfractions. This subfraction has been found to be an excellent medium for evaluating or screening tastants.

Materials for adjacent non-taste bud bearing epithelial tissue were additionally isolated by similar techniques, purified and used as controls according to the process of this invention.

To reiterate, taste receptors located in taste bud membrane served, in the evaluation process of this invention, as a medium for tastant screening. Prior research had attempted unsuccessfully to use, for example, whole papillae, as compared to receptors within the taste buds, to evaluate tastants. These results were inaccurate and unsatisfactory because the medium used in the prior art studies contained contaminants which, in addition to the receptors, also readily bind tastants. Therefore prior results were inaccurate and confused because of this contamination. Prior to this invention it was not possible to accurately evaluate taste characteristics such as the tastant-receptor binding strength, the relative number of binding sites available for a given tastant, or the relative or competitive binding activity of two different tastants, to name only a few factors influencing taste. These factors and many others may now be readily and accurately evaluated according to the process of this invention as will be subsequently explained.

It is then an essential feature of this invention to isolate and purify taste bud receptor membrane as distinguished from the epithelial tissues surrounding the taste bud and the serous and mucous glands normally present therein.

In order to isolate the receptor material the bud is initially caused to swell and open preferably by exposure to a hypotonic buffer, and to pressure. The receptor material is then excised by a selective, gentle homogenization, and filtered to isolate a receptor containing filtrate.

Following isolation of the material it is necessary to purify it to form a receptor membrane enriched medium. Purification is achieved with an initial fractionization by differential centrifugation. A purified subfraction is then isolated by sucrose gradient centrifugation. Of the subfractions formed it has been discovered that a relatively pure receptor membrane enriched subfraction may be isolated by this sucrose gradient centrifugation. The identical procedure is also carried out to isolate and purify epithelial tissue surrounding the bud for use as a control.

The receptor membrane enriched subfraction may then be used in a wide variety of taste related screening tests. It has been found for example that $^{14}C$ tastant incubated with the receptor subfraction (identified as $P_{4(B)}$ hereinafter) will reach equilibrium with said subfraction so that the quantity bound, the dissociation or binding constant, and similar data may be measured. This mixture may also be incubated with unlabeled tastant to evaluate the tightness and specificity of the tastant-receptor bond by measuring the amount of labeled tastant displaced by the unlabeled tastant. The fraction may further be incubated with two tastants to evaluate the competitive aspects of binding for relative comparison.

These and other data as will be subsequently pointed out may be derived from the enriched subfraction medium so that tastants of relative or comparative strengths and qualities may be accurately measured.

Accordingly, it is an object of this invention to provide a process for isolating and purifying taste bud receptor containing membrane for use in screening tastant materials.

It is another object to provide a process whereby taste buds may be opened to expose receptor containing material which is then removed and purified for use as a screening medium.

It is a further object of this invention to provide a process for evaluating the characteristics of taste for specific tastant materials accurately so that said materials may be screened for both quantitative and qualitative evaluations concerning the relative strength and activity thereof.

It is still a further object to provide a process whereby radioactive labeled tastant materials may be incubated with a taste bud receptor medium to form a tastant-receptor complex binding a portion of said tastant to said receptor in an equilibrium condition for quantitative evaluation of the taste characteristics of said tastant material.

These and other objects will become readily apparent with reference to the drawings and following description wherein:

FIG. 1 is a schematic diagram of coring and excision of circumvallate papilla illustrating: A. Removal of central core (coring) of papilla in order to excise central mucous gland. B. Excision of papilla from the epithelial surface of the tongue in order to remove papilla from basal serous glands. C. Resultant material from steps A and B.

Figure 2:
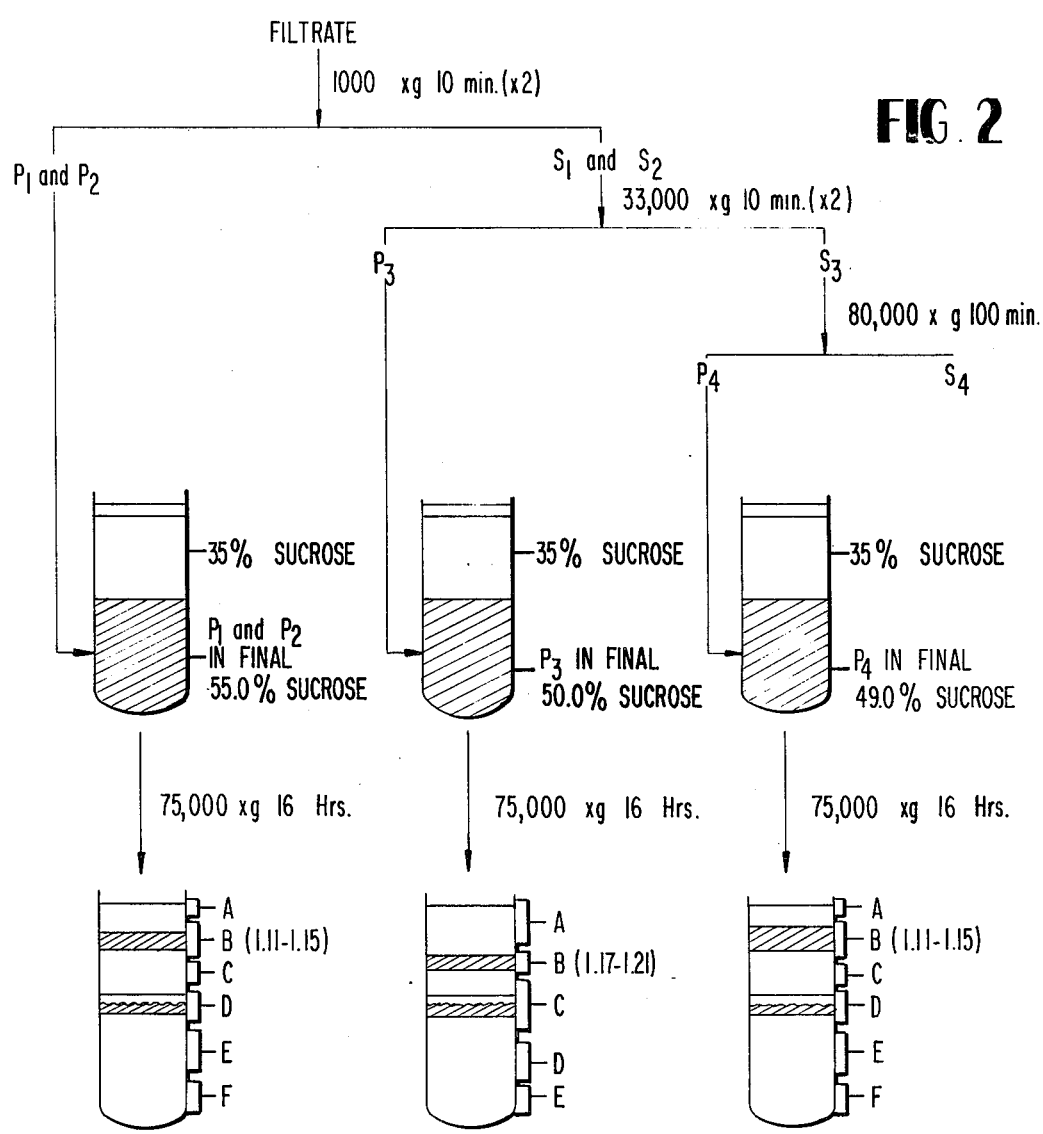

FIG. 2 is a diagram of preparation of fractions and subfractions by differential and gradient centrifugation from crude filtrates from taste bud enriched fractions from circumvallate papillae and from epithelial tissue enriched fractions from areas surrounding the circumvallate papillae.

Figure 3:
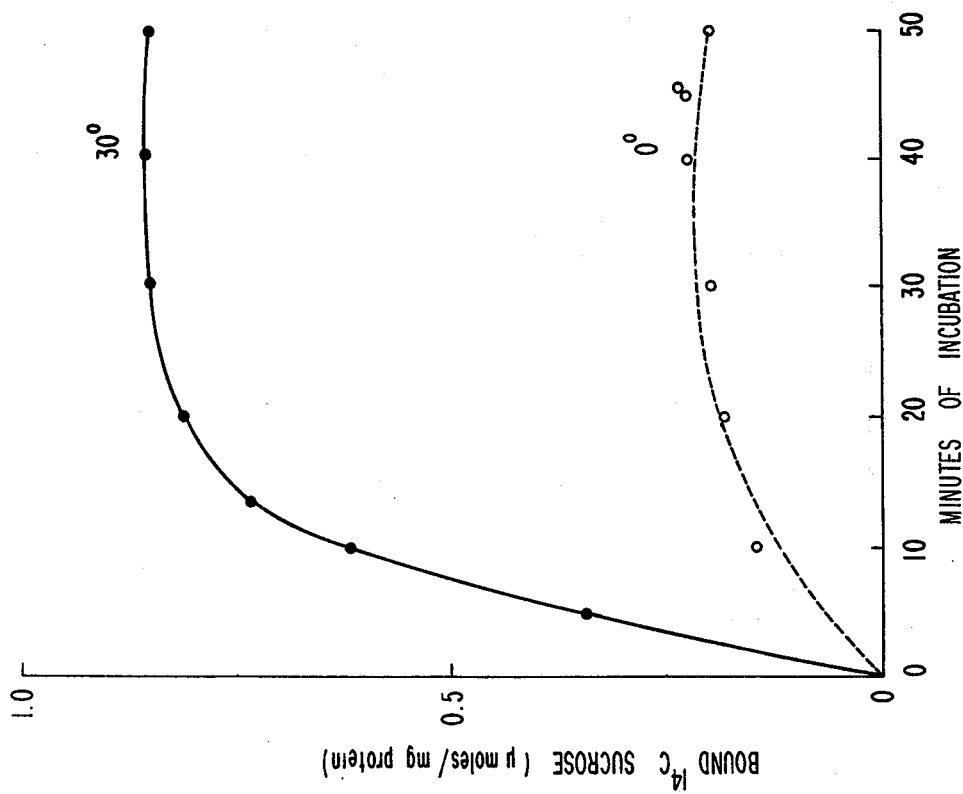
Figure 4:
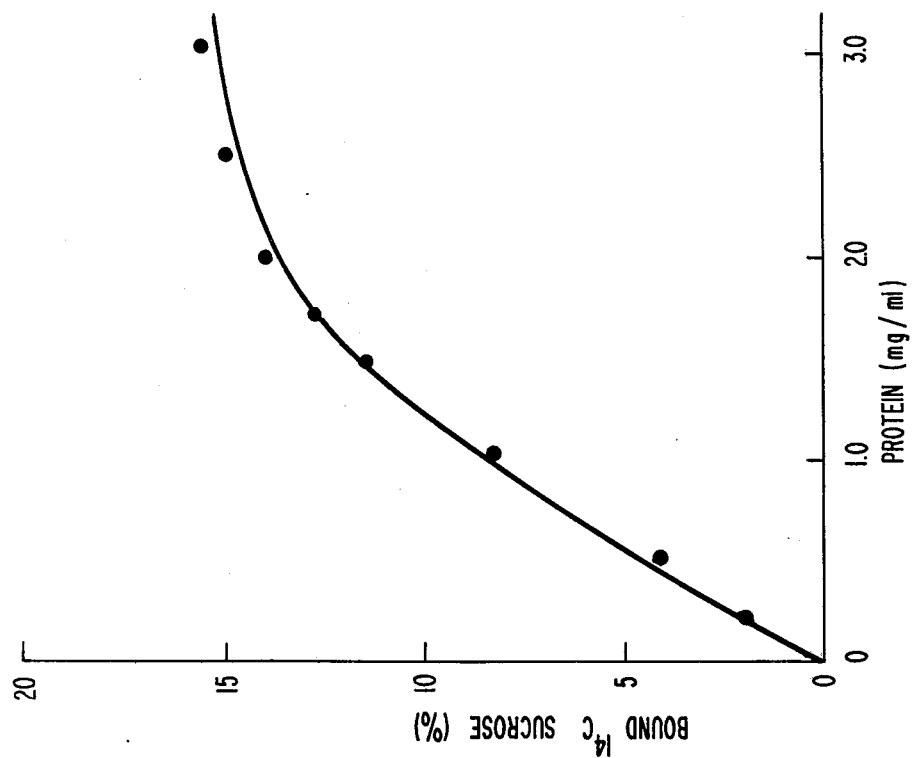
Figure 3:
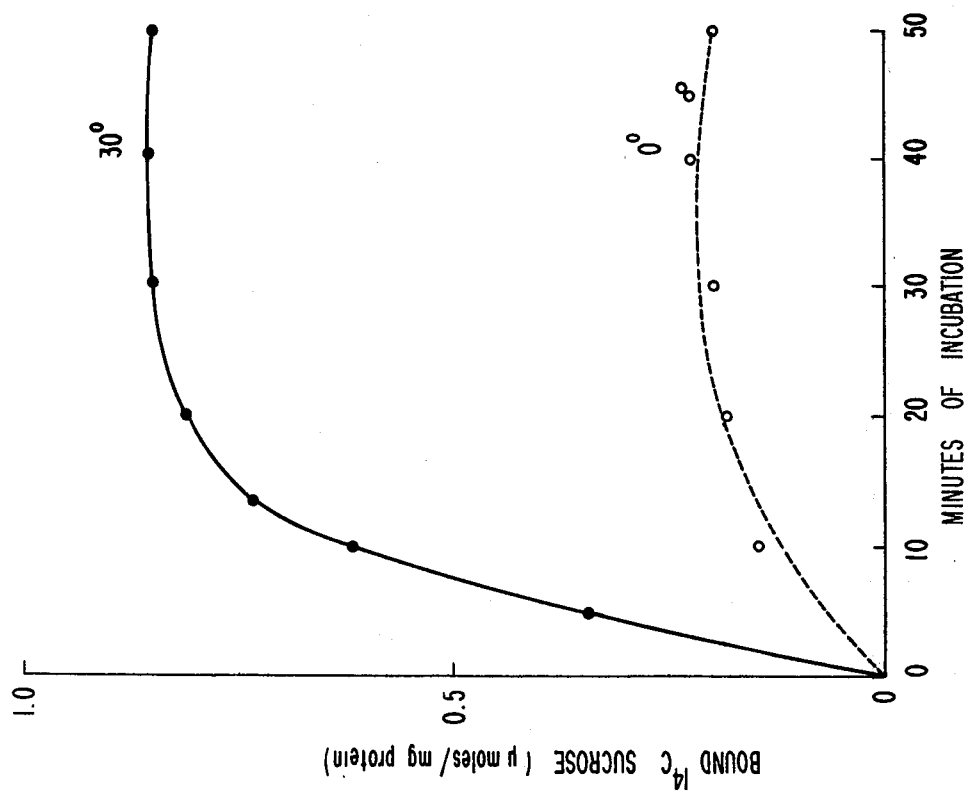

FIG. 3 illustrates the effects of temperature on $^{14}C$ sucrose binding to $P_{4(B)}$ taste bud subfractions. Incubations, at 0° and 30° with suspensions of taste bud subfractions $P_{4(B)}$ (3–5 ug protein), 26 $\mu M$ $^{14}C$ sucrose and KRB in a final volume of 100 $\mu l$. Each point is the mean of triplicate assays from two tissue preparations.

Figure 4:
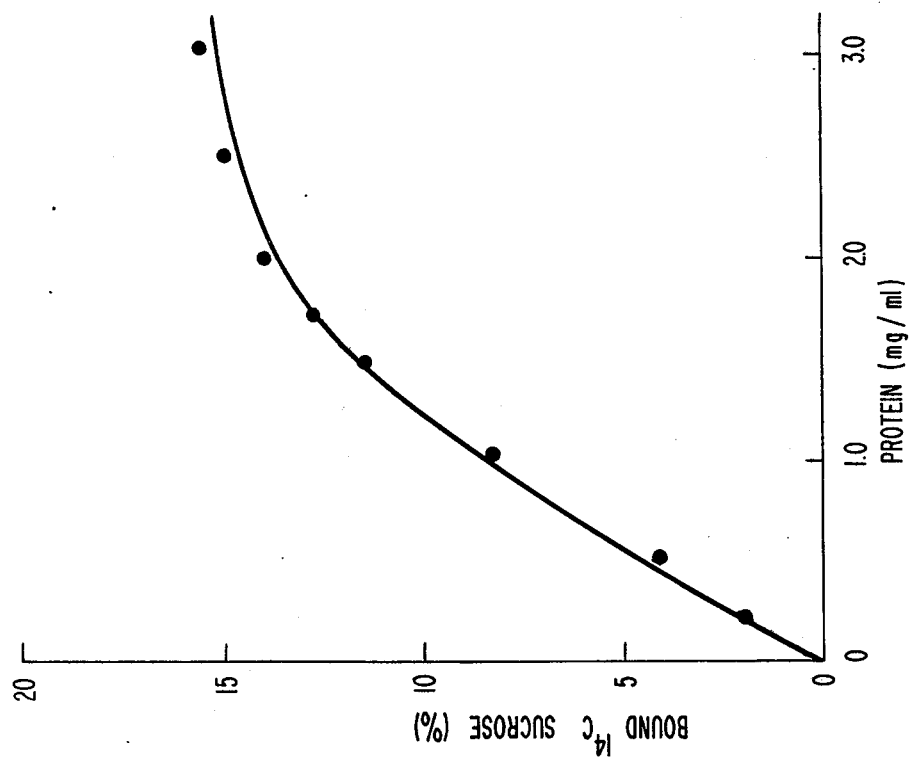

FIG. 4 illustrates the effects of protein concentration on $^{14}C$ sucrose binding to $P_{4(B)}$ taste bud subfractions. Incubations, at 30° C. for 30 min with 26 $\mu M$ $^{14}C$ sucrose, various concentrations of protein obtained from taste bud subfraction $P_{4(B)}$ and KRB in a final volume of 100 $\mu l$. Each point is the mean of triplicate assays from two tissue preparations.

FIG. 5 illustrates displacement of the initial binding of $^{14}C$ sucrose from $P_{4(B)}$ subfractions from taste bud (solid line) and non-taste bud bearing epithelial tissue (dotted line) by increasing concentrations of unlabeled sucrose. Initial sucrose concentration, 26 $\mu M$; incubation, 30 min. Each point is the mean of triplicate assays from two tissue preparations on two occasions. The ordinate represents the ratio of B (amount of $^{14}C$ sucrose bound after addition of unlabeled sucrose) to $B_o$ (amount of $^{14}C$ sucrose bound before addition of unlabeled sucrose) × 100; abscissa, concentrations of unlabeled sucrose added.

FIG. 6 illustrates the binding of $^{14}C$ sucrose to taste bud $P_{4(B)}$ subfractions and subsequent displacement with unlabeled sucrose. Initial sucrose concentration, 26 $\mu M$. Each point is the mean of triplicate assays from two tissue preparations on two occasions. At arrow, 1 mM unlabeled sucrose added. Inset illustrates semilog plot of displacement of $^{14}C$ sucrose with unlabeled sucrose over time; the ordinate represents the $^{14}C$ sucrose bound (in %) corrected for non-specific binding.

FIG. 7 illustrates the binding of $^{14}C$ labeled and unlabeled homologous sugars [sucrose (A), fructose (B), glucose (C), cyclamate (D), saccharine (E), and lactose (F)] to $P_{4(B)}$ subfractions from taste bud (solid lines and circles) and non-taste bud bearing epithelial tissue (dotted line and open circles). Ordinate, ratio of B to $B_o$ × 100 as in FIG. 3; abscissa, concentrations of unlabeled sugar added. Each point is the mean of triplicate determinations from three tissue preparations.

Figure 8:
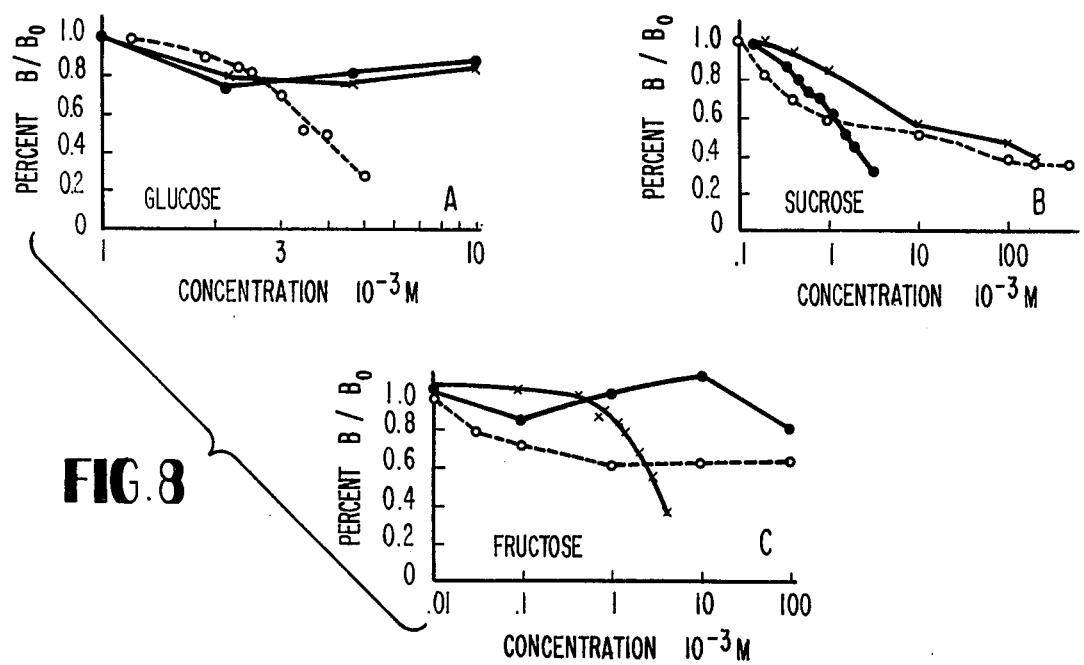

FIG. 8 illustrates the binding of $^{14}C$ labeled and unlabeled homologous and heterologous sugars to taste bud $P_{4(B)}$ subfractions. Open circles, dotted lines, glucose; closed circles, solid lines, sucrose; X's, solid lines, fructose. In A (Glucose), $^{14}C$ labeled sucrose, fructose and glucose were incubated with unlabeled glucose only; in B (Sucrose) with unlabeled sucrose only; in C (Fructose) with unlabeled fructose only. Ordinate, ratio of B to $B_o$ × 100; abscissa, concentrations of unlabeled sugar added ($10^{-1}M$ – $10^{-5}M$). Each point is the mean of triplicate assays from two tissue preparations.

FIG. 9 illustrates Scatchard plots of binding of sucrose (A), fructose (B), glucose (C), cyclamate (D) and saccharine (E) to $P_{4(B)}$ subfractions from taste bud and non-taste bud bearing epithelial tissues. The sugar noted in the upper left hand corner of each panel signifies the unlabeled sugar used in each study. Ordinate, ratio of bound radioactivity (amount of $^{14}C$ sugar bound to subfraction after incubation with the unlabeled sugar) to free radioactivity (difference between the bound radioactivity and the total radioactivity initially added); abscissa, concentrations of bound $^{14}C$ sugar.

Figure 10:
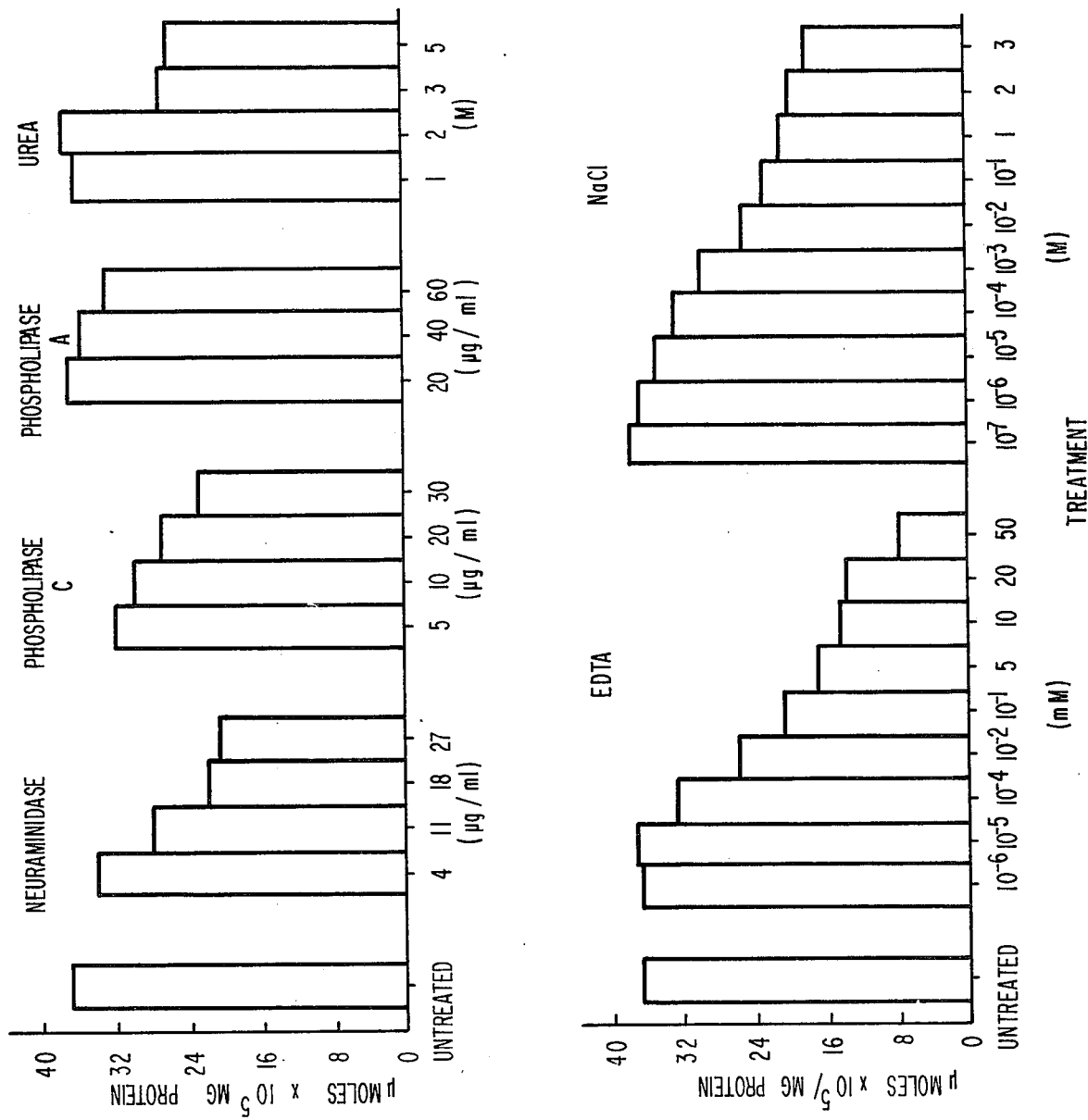

FIG. 10 illustrates the effects of neuraminidase, phosphoslipase C, phospholipase A, EDTA, NaCl and urea on binding of $^{14}C$ sucrose to taste bud $P_{4(B)}$ subfractions. Initial $^{14}C$ sucrose concentration, 26 $\mu M$. Ordinate, sucrose bound; abscissa, concentration used to inhibit binding. Each value is the mean of three determinations from two tissue preparations.

Figure 11:
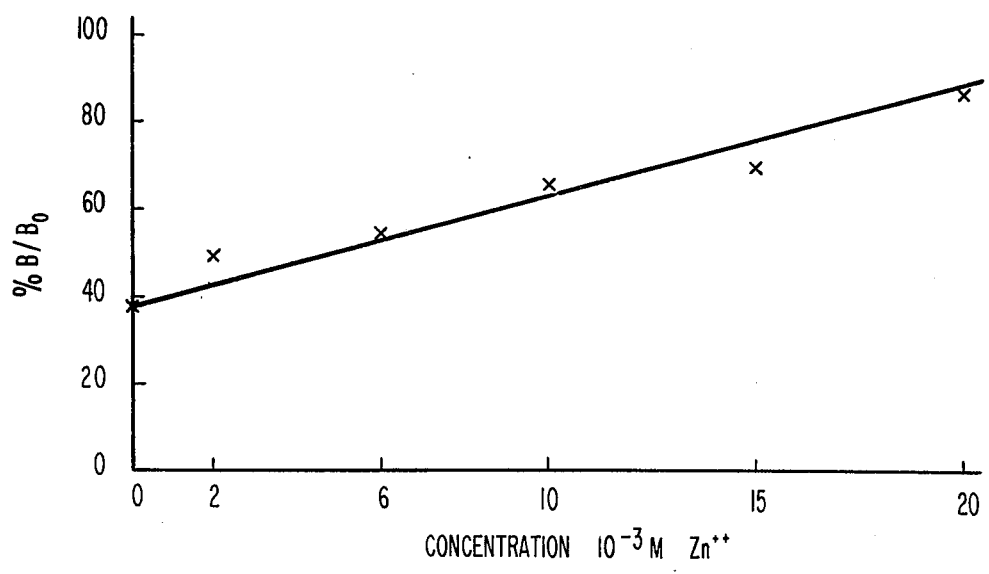

FIG. 11 illustrates the effects of $ZnCl_2$ on EDTA inhibition of $^{14}C$ sucrose binding to taste bud $P_{4(B)}$ subfractions. Initial $^{14}C$ sucrose concentration, 26 M. Ordinate, ratio of B (after incubation with 5 mM EDTA and graded concentrations of $ZnCl_2$) to $B_o$ (amount $^{14}C$ sucrose bound after incubation with 5 mM EDTA only) × 100; abscissa, concentration of added $ZnCl_2$. Each point is the mean of two determinations from two tissue preparations.

The following is a detailed description of a preferred embodiment of the process of this invention. As will be obvious to those skilled in the art, the procedure to be described is not intended to be limited to the source (bovine) of the receptors isolated, and is adaptable to any animal including human source. Furthermore while evaluations of sugars are illustrated, the procedures of this invention are intended to be adaptable to any tastant compound or material.

I. Isolation Of Taste Bud Contents

Although previous investigators have claimed to have obtained information about some chemical aspects of the taste process, it is difficult to interpret their results since their preparations consisted of homogenates of either whole tongues or whole lingual papillae of which taste buds comprise only a very small part. In order to study this problem it was first necessary to develop a procedure by which the contents of taste buds, mainly from the more apical portions, could be isolated from circumvallate papillae. The procedure for preparing the test and control tissues is as follows:

Tissue Preparation

Three bovine tongues obtained immediately after sacrifice were used. Two areas of surface epithelium from the left and right posterior surfaces of each tongue were widely excised, each area containing from ten to twenty circumvallate papillae. The four areas obtained from the first two tongues were immediately frozen on a dry ice block with the lamina propria surface adhering to the ice block. The epithelial surface was then allowed to thaw. The middle portion of each papilla was excised (cored) using a series of circular stainless steel punch instruments with external diameters ranging from 0.8 mm to 1.6 mm. With these instruments the entire internal portion of the papilla was cored without damage to the external surface as shown schematically in FIG. 1A. Each whole, intact circumvallate papilla P and its crypt was then excised from the epithelial tissue, first by using a series of circular stainless steel punch instruments with external diameters ranging from 2.0 mm to 6.0 mm (FIG. 1B) and then by surgically excising the papilla from its epithelial base (FIG. 1C). The excised papillae were then treated as outlined in Table I (Groups 1–5).

TABLE I

Preparation and Isolation of Taste Bud Contents from Bovine Circumvallate Papillae

| Circumvallate Papillae | Untreated | Freezing in Dry Ice | Coring | Hypotonic Swelling[+] | Nitrogen Pressurization[++] | Homogenization[*] |
|---|---|---|---|---|---|---|
| GROUP | | | | | | |
| 1 | + | | | | | |
| 2 | | + | + | | | |
| 3 | | + | + | + | | |
| 4 | | + | + | + | + | |
| 5 | | + | + | + | + | + |

[+] 0.005 M Tris-MCl buffer, pH 8.0 at 4° C. for 30 minutes.
[++] 900 psi in a precooled Cell Disruption Bomb for 3 min at 4° C. (X 3).
[*] Fifteen complete strokes with a motor driven teflon pestle (external diameter 1.9 cm) at 1000 rpm in a loose fitting glass homogenizer (internal diameter 2.7 cm) at 4° C.

These cored, excised papillae and their crypts were divided into groups of five each. One group of five (Group 2, Table I) immediately after excision was placed into cold 3% glutaraldehyde and examined by light and electron microscopy. Another group of five (Group 3, Table I) immediately after excision was placed into hypotonic, 0.005 M Tris-HCl buffer, pH 8.0, at 4° C. for 3 min., removed, rinsed twice with cold working solution (unbuffered 0.3 M sucrose in 1 mM $CaCl_2$, adjusted to pH 7.4) and placed in cold 3% glutaraldehyde for examination by light and electron microscopy. Another group of five (Group 4, Table I) immediately after excision was treated by hypotonic swelling, as in Group 3, but was placed into a 5 ml beaker containing 2 ml working solution. This beaker was placed into a precooled Cell Disruption Bomb (Parr Instrument Co., Moline, Illinois) at 4° C. Nitrogen pressure of 900 psi was applied through the dump valve connected to the gas filling valve. This procedure was repeated 3 times. Following these procedures these papillae were placed into cold 3% glutaraldehyde for examination by light and electron microscopy. Another group of five (Group 5, Table I) immediately after excision was treated by hypotonic swelling and nitrogen pressurization, as in Group 4, but then was placed into a glass homogenizer (internal diameter 2.7 cm) containing 3 volumes of working solution, and subjected to 15 complete strokes with a motor driven teflon pestle (external diameter 1.9 cm) at a speed of 1000 rpm at 4° C. The resulting suspension was filtered through two layers of 0.1 mm nylon mesh gauze. The retained, treated papillae as well as the filtered material was each placed into cold 3% glutaraldehyde and examined by light and electron microscopy. The filtrate was pelleted by centrifugation at 100,000 × g for 60 minutes and random samples taken for examination by electron microscopy.

The two epithelial areas obtained from the third tongue were neither frozen nor centrally cored with punch instruments. Instead, five whole, intact papillae and their crypts were surgically excised following use of the larger diameter circular stainless steel punch instruments (2–6 mm) and placed immediately into cold 3% glutaraldehyde (Group 1, Table I) and examined by light and electron microscopy.

Anatomical Examination

Three circumvallate papillae and their crypts from Groups 1, 2 and 3 and all papillae from Groups 4 and 5 were prepared for electron microscopic examination. Papillae were post-fixed in 1% osmium tetroxide in phosphate buffer, pH 7.2, dehydrated in graded alcohol (25–100%) and propylene oxide, and embedded in Epon-Araldite. Thin (60 mu) sections were cut on a Porter-Blum MT-2 ultramicrotome, stained with lead citrate and uranyl acetate and examined in an RCA EMU-3E electron microscope.

Circumvallate papillae and their crypts were prepared for examination by light microscopy in two ways. Two papillae from Groups 1, 2 and 3 were placed in paraffin, cut in 5μ sections, mounted on glass slides and examined after staining with hematoxylin eosin. The papillae prepared for electron microscopic examination were cut in thick (5μ) sections on a Porter-Blum microtome and stained with toluidine blue. In these latter papillae thick and thin sections were always cut in continuity.

Taste buds were observed either on the papillary surface of the crypt or, less commonly, in the stratified squamous epithelium on the lingual surface of the papilla. Serous glands, commonly present in the lowest portion of the papilla, beneath the taste bud bearing epithelial areas, were excluded from the excised papillae by the surgical techniques used.

The circumvallate papillae and taste buds from Groups 2 and 3 were found not to differ in anatomical appearance from those of Group 1 except that the central mucous gland had been cored. Examination of papillae from Group 4 treated by freezing, coring, hypotonic buffer and nitrogen pressurization indicated that the papillae and the taste buds retained a structural appearance which cannot be differentiated from those of Groups 1, 2 or 3 by light or electron microscopy. Following treatment of papillae with freezing, hypotonic buffer, nitrogen pressurization and selective homogenization (Group 5) numerous large vacuoles were observed in the taste buds indicating loss of cellular contents, and anatomical changes in the epithelial tissue immediately surrounding the taste buds was not observed. Electron microscopic examination of taste buds from papillae of Group 5 compared with those from untreated, control papillae (Group 1) or from treated papillae without homogenization (Group 4) indicated that some of the contents of the taste buds had been extruded, mainly from the more apical region; no anatomical change in the epithelial tissue immediately surrounding the taste buds was observed in any of these papillae. The cells in the more basal portion of the buds from papillae of Group 5, in general, retained their normal cellular architecture although the nuclei were less darkly stained than in control buds and some intra- and extra-cellular vacuoles were observed.

The pelleted filtered extract containing material separated from the taste buds was also examined by electron microscopy. It consisted of cellular debris in which fine filaments, intact membranes and membrane fragments, vesicles, ribosomes and occasional centrioles could be recognized.

In summary then, the specific techniques developed to excise circumvallate papillae from the lingual surface without damaging their taste buds and to separate the taste bud bearing portion of the papilla from the normally present mucous and serous glands was in part accomplished, after freezing the papillae, by coring the center with a stainless steel punch which removed the central mucous gland. This separation was completed following total surgical excision of the remaining papilla thereby removing it from the surrounding epithelial tissue; this removed the papilla from the serous glands which lie, in situ, beneath the base of the papillary crypts.

Selective homogenization procedures were evaluated using a graded series of speeds and number of applications of the teflon pestle to the glass homogenizer tube. These results, also evaluated by light microscopy, indicated that as pestle speeds rose above 1000 rpm or as more than 15 complete pestle strokes were used increasingly severe damage to the surrounding epithelium as well as extraction of increasing amounts of taste bud contents occurred. The procedure adopted (Table I, Group 5) was chosen because it was not associated with anatomical changes in the epithelium surrounding the taste buds and produced only little to moderate damage to the more basal areas of the taste buds themselves.

II. Isolation Of Fractions From Filtrates From Circumvallate Papillae And From Surrounding Epithelial Tissue A filtered homogenate (filtrate) was obtained from approximately 800 cored taste bud containing circumvallate papillae (6 gm wet weight) excised from 40 bovine tongues following placement in hypotonic buffer, nitrogen pressurization and selective homogenization according to the above procedure (Group 5). A filtrate was also obtained from epithelial tissue (6 gm wet weight) which immediately surrounded the excised circumvallate papillae. This epithelial tissue contained neither papillae nor taste buds as determined by light microscopy. The epithelial tissue was treated, as were the papillae, by placement in hypotonic buffer, nitrogen pressurization and selective homogenization to obtain the filtrate.

With reference to FIG. 2, differential centrifugation of the filtrates from taste buds and epithelial tissue was carried out by the method of Touster et al (1970) J. Cell. Biol. 47, 604–618. Initially the filtrates were centrifuged at 1000 xg for 10 min. [Sorvall rotor (S.S. 34)]. The supernatant fluids ($S_1$) were saved. The 1000 xg pellets ($P_1$) were resuspended by mixing in three volumes of "working solution" (unbuffered 0.3 M sucrose in 1 mM $CaCl_2$, pH 7.4) and centrifuged as above. The 1000 xgpellets ($P_2$) were separated from the supernatant ($S_2$) and saved. The combined supernatants ($S_1$ and $S_2$) were centrifuged at 33,000 xg for 8 min. [Sorvall rotor (S.S. 34), brake off]. The supernatants from this centrifugation were removed by aspiration. The pellets were resuspended and centrifuged again at 33,000 xg. The pellet from this centrifugation was saved ($P_3$). The supernatant from this centrifugation was combined with that obtained from the prior centrifugations ($S_3$). These supernatants ($S_3$) were centrifuged at 80,000 xg for 100 min. (Beckman S.W. 30 rotor). The resulting final supernatants ($S_4$) were removed, leaving a white loosely packed layer on top of the final pellets ($P_4$).

Preparation of Subfractions From $P_2$, $P_3$ and $P_4$ Fractions By Sucrose Gradient Centrifugation Sucrose gradient centrifugation of the fractions were carried out by the method of Touster with slight modifications. Each fraction was suspended in 5 ml of working solution in a cellulose nitrate tube (34 ml tube capacity per bucket). A 70% (W/W) sucrose solution was then added until final sucrose concentrations of 55.0± 1% (W/W), 50.0± 1% (W/W) and 49.0 ± 0.5% (W W), were obtained from fractions $P_2$, $P_3$ and $P_4$, respectively, determined by refractometry. A 35.0% sucrose solution was layered above each sample and enough working solution layered above this to yield a total volume of 32 ml. After centrifugation at 75,000 xg for 16 hr. (Beckman S.W. 25.1 rotor) the sucrose gradient was separated with a Buchler polystatic pump.

Sucrose gradient solutions were prepared by percentage by weight of sucrose, the final values checked at 25° in an Abbe-3L-refractometer (Bausch and Lomb, Inc., Rochester, N.Y.) and corrected to 5° C. All centrifugal forces were those at the center of the centrifuge tube and all centrifugations were performed at 5° C.

Density of each fraction was determined by refractometry in an Abbe-3L-refractometer at 5° C. and by Micule Density Markers (Beckman Co. #858485).

Means and standard errors were calculated for each measurement from three determinations of three separate preparations of bovine tongues (40 tongues were processed per preparation) from each fraction of taste bud and epithelial tissue except where specifically indicated. Significance of differences between the various measurements was determined by the Student t test.

Each fraction and subfraction was examined both by phase-contrast microscopy and by electron microscopy during each step of the procedure. For examination by electron microscopy pellets from both papillae and epithelial fractions were fixed in 1% osmium tetroxide in phosphate buffer, pH 7.2, dehydrated in graded alcohols (25–100%) and propylene oxide, and embedded in Epon-Araldite. Several sections were prepared at random through the entire pellet on a Porter-Blum MT-2 ultramicrotome and examined in an RCA EMU-3E electron microscope.

Chemical Analysis

The following were assayed: protein, total cholesterol and cholesterol esters with crystalline galactosamine hydrochloride (Sigma) as standard; total hexose by the anthrone reaction; nucleic acids were extracted and DNA and RNA measured; total lipids were extracted and phospholipids determined; dry weight was determined in each sample by suspension in distilled water, centrifugation four times at 100,000 × g for two hours, the resulting pellet dried overnight in vacuo over Aquasorb (Mallinckrodt, St. Louis) and weighed until constant on an electrostatic balance.

Enzyme Analyses

The following enzymes were assayed; succinic cytochrome-c-reductase; glucose-6-phosphatase, modified by preincubation for 15 min. at pH 9.0 with 5 mM cysteine, 5 mM dithiothreitol and 5 mM EDTA; acid phosphatase at pH 4.8; ($Na^+ + K^+$), $Mg^{++}$ ATPase; 5'-nucleotidase modified by preincubation for 15 min. at pH 9.1 with 5 mM cysteine and 5 mM dithiothreitol; esterase with p-nitrophenyl acetate (Sigma) as substrate; alkaline phosphatase with 1 mM p-nitrophenyl phosphate (Sigma) as substrate in the presence of 2.5 mM $MgCl_2$ and 0.02 M Tris-HCl, pH 9.0, in a final volume of 0.5 ml.

Density Distribution Of Taste Bud And Epithelial Tissue Subfractions

Two visible bands were present in each of the taste bud fractions ($P_2$, $P_3$, $P_4$) after sucrose gradient centrifugation (FIG. 2). The upper visible bands, called B [hence subfractions $P_{2(B)}$, $P_{3(B)}$ and $P_{4(B)}$] appeared as white particulates. These bands in subfractions $P_{2(B)}$ and $P_{4(B)}$ had the same density [1.15 ± 0.01, 1.15 ± 0.02, respectively (mean ± 1 SEM]; this band in subfraction $P_{3(B)}$ had a slightly higher density (1.19 ± 0.02). The lower visible bands, called D [hence subfractions $P_{2(D)}$, $P_{3(D)}$ and $P_{4(D)}$] were broader, of a pale pink color and had higher densities than did the upper bands [1.20 ± 0.02, 1.25 ± 0.02, 1.27 ± 0.03, $P_{2,3,4(D)}$, respectively]. At the bottom of each centrifuge tube a light, white precipitate, called F [hence subfractions $P_{2,3,4(F)}$] was observed.

The bands in subfractions $P_2$ and $P_4$ obtained from epithelial tissue fractions were similar in appearance to corresponding taste bud subfractions. At the upper part of their respective sucrose gradients subfractions $P_{2(B)}$ and $P_{4(B)}$ appeared as white bands but they were significantly less dense (1.06 ± 0.01, 1.10 ± 0.01, respectively) and the particulate band fractions narrower than corresponding taste bud subfractions. No clearly defined subfraction was observed in the upper part of the epithelial tissue $P_3$ fraction after sucrose gradient centrifugation; only occasional clusters of white particles were observed. At the lower part of their respective sucrose gradients subfractions $P_{2,3,4(D)}$ appeared as pale pink bands with higher densities (1.21 ± 0.04, 1.24 ± 0.01, respectively) than observed in corresponding $P_{(B)}$ subfractions. These bands were as dense and as broad as corresponding taste bud subfractions. Taste bud and epithelial subfractions $P_{2,3,4(F)}$ were denser than any other subfraction analyzed ranging from 1.33–1.35.

Microscopic Analyses

Pellets from crude filtrates from taste bud and epithelial tissue indicated that both contained many fine filaments, mitochondria, dense bodies, ribosomes, vesicles and membranes; however, the epithelial tissue filtrate consisted mainly of fibrous material, the tissue from papillae exhibiting a greater number of membrane fragments. In addition, centrioles were observed only in the papillae filtrates. Differences in the morphological characteristics of taste bud and epithelial subfractions $P_{2,4(B)}$ were also observed. Each taste bud subfraction contained many broken plasma membrane ghosts with some contamination with ribosomes and broken mitochondria but no evidence of other cellular structures, dense bodies or filamentous material. Visual examination suggested that taste bud subfraction $P_{4(B)}$ contained more membranes and had less contamination than did subfractions $P_{2,3(B)}$. Subfractions $P_{2,4(B)}$ from epithelial tissue are difficult to interpret due to the presence of large amounts of filamentous material; however, occasional broken membrane vesicles and ribosomal particles were observed. There was then a relative enrichment of membranes in taste bud subfractions over that of epithelial tissue subfractions.

Differences in composition of subfractions $P_{2,3,4(D)}$ isolated from taste bud and from epithelial tissue fractions were also observed. Although broken plasma membranes were found in each taste bud subfraction each contained fewer membranes than found in corresponding B subfractions along with many other cellular organelles (FIG. 5). D subfractions from epithelial tissue fractions, as in B subfractions, contained much filamentous, fibrous tissue and were difficult to interpret; however, occasional broken membrane vesicles were observed, mainly in subfractions $P_{3,4(D)}$ as well as many other cellular organelles (FIG. 5). Subfractions $P_{2,3,4(F)}$ from taste bud and epithelial fractions contained mainly large cellular fragments and small pieces of tissue.

ENZYMATIC ANALYSES

Distribution, recovery and specific activity of each enzyme studied in the fractions ($P_2$, $P_3$, $P_4$, $S_4$) and in the subfractions [$P_{2,3,4(B)}$; $P_{2,3,4(D)}$] isolated from taste bud and epithelial tissue are summarized in Tables II--IV. Subfractions $P_{2,3,4(F)}$ were not systematically studied since their contents consisted mainly of large cellular fragments and debris.

Recoveries of all enzyme activities isolated from both taste bud and epithelial tissue were similar, ranging from 67% to 100% (Table II); however, maximum enzyme activity for each tissue was differentially distributed in the four major fractions isolated, as expected.

Distribution and specific activities of enzymes isolated in subfractions $P_{2,3,4(B)}$ (Table III) and $P_{2,3,4(D)}$ (Table IV) show significant differences from the filtrate for some enzymes, particularly those previously associated in other tissues with enriched plasma membranes; significant differences between enzyme activities obtained from taste bud and epithelial tissue were also observed.

For $Na^+ + K^+$ ATPase specific activity of taste bud subfractions $P_{2(B)}$ and $P_{4(B)}$ was significantly higher [$p < 0.01\ P_{2(B)}$, $P < 0.05\ P_{4(B)}$] than in the filtrate (Table III); there was no change in specific activity of corresponding epithelial subfractions. Activity in taste bud subfractions $P_{2(B)}$ was significantly greater ($p < 0.01$) than in epithelial subfraction $P_{2(B)}$ (Table III). For $Mg^{++}$ATPase, specific activity in taste bud fractions $P_{3,4(B)}$ were significantly ($p < 0.01$) higher than in the filtrate (Table III) whereas in the epithelial fractions it was lower than in the filtrate; activity of taste bud subfractions $P_{2,4(B)}$ was significantly higher ($p < 0.01$) than in corresponding epithelial subfractions (Table II).

For alkaline phosphatase specific activity of each B taste bud subfraction increased significantly ($p < 0.001$) with respect to the filtrate although the greatest increase, approximately 12 fold, was in subfraction $P_{4(B)}$; there was no change in activity in corresponding epithelial subfractions (Table III). Activity recovered in taste bud subfractions $P_{2,4(B)}$ were significantly higher [$p = 0.05$, $P_{2(B)}$, $p < 0.001$, $P_{4(B)}$] than in corresponding epithelial tissue subfractions (Table III).

For esterase specific activity in each $B$ taste bud subfraction was significantly higher ($p < 0.001$) than in the initial filtrate or in corresponding epithelial subfractions (Table II); in taste bud subfraction $P_{4(B)}$ the specific activity increase was the greatest with respect to the initial filtrate, approximately 11 fold.

For protein, approximately twice as much was recovered from the crude taste bud filtrate as from the corresponding epithelial filtrate (Table V); for membrane protein, the basis of comparison of the chemical composition of taste bud and epithelial subfractions (Tables VI and VII) approximately twice as much was also recovered in the taste bud subfractions as from the corresponding epithelial tissue subfractions (Table VII). All protein recovered from $B$ taste bud subfractions was approximately eight times higher than that recovered in corresponding epithelial subfractions (Table V). The number of taste buds in the original sample of 40 cow tongues was estimated at 40,000, based upon an average of 20 papillae excised from each tongue, an average of 50 taste buds per papilla and recovery from each bud by the isolation process estimated at approximately one-third of the taste bud volume. From these estimates it was predicted that approximately 50 mg of protein could be isolated in the original filtrate. This estimate agrees reasonably well with the protein actually recovered in the original filtrate (Table V).

Chemical Composition

Phospholipid, cholesterol, total hexose, hexosamine, sialic acid, DNA and RNA concentrations in corresponding taste bud and epithelial $_B$ subfractions are shown in Table VI. Except for total hexose and RNA content of the $P_{4(B)}$ subfraction, the phospholipid, cholesterol, hexosamine, sialic acid, DNA and RNA concentrations of the B taste bud subfractions were significantly higher ($p < 0.001$) than in corresponding epithelial subfractions.

The protein, lipid, cholesterol and phospholipid concentrations from corresponding taste bud and epithelial B subfractions and the ratios of protein to lipid and cholesterol to phospholipid are shown in Table VII. Protein and cholesterol concentrations of each taste bud subfraction were higher than those in corresponding epithelial subfractions. Similarly, protein/lipid ratios of B taste bud subfractions were three times higher than those for epithelial subfractions, whereas cholesterol/phospholipid ratios in taste bud subfractions were twice as high.

TABLE II

Distribution of Enzyme Protein and Activity in each Fraction Isolated from Epithelial Tissue Enriched Filtrates Surrounding Bovine Circumvallate Papillae

| Fraction* | | $P_2$[1] | $P_3$ | $P_4$ | $S_4$ | Recovery |
|---|---|---|---|---|---|---|
| Protein[2] | Bud[3] | 17.3 ± 3.4 | 25.2 ± 4.8 | 24.3 ± 4.6 | 30.0 ± 7.4 | 97 ± 8 |
| | Epi | 17.0 ± 1.2 | 14.8 ± 0.8 | 13.9 ± 1.1 | 52.3 ± 17.2 | 98 ± 4 |
| Acid Ptase | Bud | 9.0 ± 2.6 | 56.2 ± 9.4 | 12.2 ± 1.9 | 5.8 ± 1.2 | 83 ± 5 |
| | Epi | 2.2 ± 0.4 | 47.2 ± 9.3 | 5.3 ± 1.4 | 27.3 ± 7.8 | 82 ± 5 |
| Succinic Cyto-c-Reductase | Bud | 3.6 ± 0.5 | 69.1 ± 8.7 | 11.3 ± 0.8 | 4.1 ± 0.6 | 88 ± 8 |
| | Epi | 2.1 ± 0.6 | 23.4 ± 4.3 | 10.8 ± 3.5 | 48.7 ± 10.4 | 85 ± 4 |
| Clu-6-Ptase | Bud | 6.2 ± 1.3 | 12.4 ± 4.6 | 41.3 ± 5.9 | 8.1 ± 1.1 | 68 ± 9 |
| | Epi | 9.3 ± 2.4 | 25.6 ± 6.9 | 19.8 ± 6.7 | 29.3 ± 5.7 | 84 ± 5 |
| $(Na^+ + K^+)ATPase$ | Bud | 10.9 ± 1.4 | 28.6 ± 6.9 | 17.4 ± 2.0 | 23.8 ± 1.9 | 81 ± 4 |
| | Epi | 7.1 ± 1.8 | 31.4 ± 9.3 | 5.1 ± 2.0 | 45.4 ± 10.3 | 89 ± 3 |
| $(Mg^{++})ATPase$ | Bud | 9.5 ± 1.0 | 32.6 ± 6.9 | 13.7 ± 2.2 | 19.2 ± 1.2 | 75 ± 3 |
| | Epi | 3.1 ± 1.2 | 40.2 ± 8.7 | 1.9 ± 0.5 | 38.8 ± 7.4 | 84 ± 6 |
| Alkaline Ptase | Bud | 13.2 ± 1.6 | 30.0 ± 2.8 | 25.4 ± 3.5 | 15.1 ± 2.9 | 84 ± 5 |
| | Epi | 8.7 ± 1.3 | 26.4 ± 5.2 | 21.2 ± 4.8 | 17.7 ± 2.3 | 74 ± 3 |
| 5'Nucleotidase | Bud | 20.4 ± 1.9 | 12.1 ± 4.7 | 23.5 ± 6.2 | 11.0 ± 2.1 | 67 ± 5 |
| | Epi | 14.5 ± 3.1 | 23.2 ± 6.4 | 1.1 ± 0.3 | 29.2 ± 6.4 | 68 ± 3 |
| Esterose | Bud | 2.12 ± 2.3 | 12.6 ± 7.8 | 34.2 ± 5.4 | 34.1 ± 9.2 | 102 ± 8 |
| | Epi | 8.7 ± 2.1 | 34.0 ± 6.9 | 9.3 ± 2.4 | 46.0 ± 7.5 | 98 ± 4 |

*Results are expressed in % of the total enzyme units present in the filtrate.
[1]$P_2$, $P_3$, $P_4$ and $S_4$ are fractions obtained from taste bud or epithelial tissue enriched filtrates by differential centrifugation.
[2]Percent values for protein concentration and specific enzymes (units) were obtained from two determinations from each of four separate preparations and expressed as M ± SFM.
[3]Bud- Taste bud
Epi- Epithelial tissue

TABLE III

DISTRIBUTION AND SPECIFIC ACTIVITY OF ENZYME IN SUBFRACTIONS P 2,3,4(B) ISOLATED FROM BOVINE TASTE BUDS AND FROM SURROUNDING EPITHELIAL TISSUE

| Enzyme | | Filtrate | SPECIFIC ACTIVITY[1] Membrane Fractions[2] | | | % RECOVERY[3] Membrane Fractions | | | All Fractions Combined |
|---|---|---|---|---|---|---|---|---|---|
| | | | $P_{2(B)}$ | $P_{3(B)}$ | $P_{4(B)}$ | $P_{2(B)}$ | $P_{3(B)}$ | $P_{4(B)}$ | |
| Acid Ptase | Bub[4] | .78 ± .12[5] | .34 ± .09(0.4)[6] | .20 ± .00(0.3) | .23 ± .05(0.3) | .50 ± .11 | .35 ± .05 | .34 ± .06 | 83 ± 3[7] |
| | Epi | .56 ± .15 | .19 ± .04(0.3) | —[8] | .12 ± .06(0.2) | .33 ± .15 | — | .20 ± .11 | 82 ± 5 |
| Succinic | Bud | .71 ± .08 | .09 ± .01(0.1) | .25 ± .07(0.4) | .04 ± .01(0.06) | 2.20 ± .52 | 6.40 ± .44 | 1.10 ± .20 | 88 ± 2 |
| Cyto-c-Reductase | Epi | .25 ± .05 | .01 ± .01(0.04) | — | .03 ± .01(0.1) | .60 ± .02 | — | 1.80 ± .30 | 85 ± 4 |
| Glu-6-Ptase | Bud | .84 ± .13 | .21 ± .09(0.2) | .15 ± .03(0.2) | .24 ± .16(0.3) | 2.00 ± .87 | 1.40 ± .44 | 2.32 ± .90 | 68 ± 9 |
| | Epi | .75 ± .21 | .09 ± .04(0.1) | — | .20 ± .08(0.3) | .50 ± .10 | — | 1.13 ± .24 | 84 ± 5 |
| $(Wa^+ + K^{30})ATPase$ | Bud | .24 ± .04 | .62 ± .11(2.6) | .36 ± .07(1.5) | .42 ± .08(1.8) | 4.30 ± 1.20 | 2.48 ± .34 | 3.00 ± .02 | 81 ± 4 |
| | Epi | .22 ± .10 | .15 ± .08(0.7) | — | .34 ± .11(1.5) | .71 ± .12 | — | 1.50 ± .09 | 89 ± 3 |
| $(Mg^{++})ATPase$ | Bud | .92 ± .10 | .97 ± .14(1.1) | 2.11 ± .62(2.3) | 2.90 ± .56(3.2) | .60 ± .08 | 1.25 ± .14 | 1.76 ± .61 | 75 ± 3 |
| | Epi | 1.12 ± .37 | .15 ± .11(0.1) | — | .72 ± .21(0.6) | .11 ± .02 | — | .60 ± .10 | 84 ± 6 |
| Alkaline Ptase | Bud | .14 ± .04 | .41 ± .04(2.9) | .45 ± .06(3.2) | 1.68 ± .51(12.0) | 2.49 ± .34 | 2.75 ± .31 | 10.32 ± .80 | 84 ± 5 |
| | Epi | .20 ± .08 | .18 ± .08(0.9) | — | .12 ± .06(0.6) | .90 ± .35 | — | .60 ± .10 | 74 ± 3 |
| 5'Nucleotidase | Bud | .85 ± .12 | .54 ± .08(0.6) | .93 ± .08(1.1) | 1.51 ± .42(1.8) | 2.02 ± .75 | 3.70 ± .61 | 5.99 ± .132 | 67 ± 5 |
| | Epi | 1.10 ± .34 | .24 ± .11(0.2) | — | 1.11 ± .20(1.0) | .10 ± .04 | — | .50 ± .12 | 68 ± 3 |
| Esterase | Bud | .23 ± .05 | 1.04 ± .27(4.5) | .64 ± .07(2.8) | 2.52 ± .82(11.0) | 3.78 ± 1.27 | 2.35 ± .42 | 9.24 ± 2.11 | 101 ± 10 |
| | Epi | .14 ± .09 | .27 ± .07(1.9) | — | .21 ± .04(1.5) | .81 ± .14 | — | .63 ± .20 | 98 ± 4 |

[1]Specific enzyme activity is expressed as μmoles of substrate altered per hour per mg protein.
[2]Taste bud and epithelial subfractions [$P_{2(B)}$, $P_{3(B)}$, $P_{4(B)}$] were obtained following differential and gradient centrifugation. See Methods.
[3]For each cellular fraction % recovery is relative to respective $P_2$, $P_3$ and $P_4$ fractions and is based on the recovery from the filtrate as 100%.
[4]Bud- Taste bud; Epi- Epithelial tissue.
[5]M ± 1 SEM of three determinations from each of three separate preparations.
[6]() - Relative specific activity calculated as specific activity of each subfraction relative to the specific activity of the filtrate.
[7]Percent protein recovered in $P_{2(B)}$, $P_{3(B)}$ and $P_{4(B)}$ respective to the taste bud $P_2$, $P_3$ and $P_4$ fractions were .04%, .12% and .17% respectively; for $P_{2(B)}$ and $P_{4(B)}$ epithelial subfractions % protein recovered was .01% and .02%, respectively.
[8]No $P_{3(B)}$ subfraction isolated from $P_3$ epithelial tissue fraction.

TABLE IV
DISTRIBUTION AND SPECIFIC ACTIVITY OF ENZYMES IN SUBFRACTIONS $P_{2,3,4(D)}$ ISOLATED FROM BOVINE TASTE BUDS AND FROM SURROUNDING EPITHELIAL TISSUE

| Enzyme | | Filtrate[5] | SPECIFIC ACTIVITY[1] Membrane Fractions[3] | | | % RECOVERY[2] Membrane Fractions | | | All Fractions Combined |
|---|---|---|---|---|---|---|---|---|---|
| | | | $P_{2(D)}$ | $P_{3(D)}$ | $P_{4(D)}$ | $P_{2(D)}$ | $P_{3(D)}$ | $P_{4(D)}$ | |
| Acid Ptase | Bud[4] | .78 ± .12 | 5.78 ± 1.72(7.4) | 30.46 ± 9.42(43.9) | 3.96 ± 1.96(5.1) | 8.50 ± 2.53 | 49.21 ± 10.41 | 5.82 ± 2.88 | 83 ± 3 |
| | Epi | .56 ± .15 | 1.36 ± .63(2.4) | —[7] | — | 2.37 ± 1.10 | — | — | 82 ± 5 |
| Succinic | Bud | .71 ± .08 | .08 ± .02(0.1) | 2.26 ± 1.21(3.2) | .22 ± .04(0.3) | 1.39 ± 1.02 | 55.31 ± 15.63 | 5.34 ± .85 | 88 ± 2 |
| Cyto-c-Reductase | Epi | .25 ± .05 | .04 ± .02(0.2) | — | — | 2.16 ± .68 | — | — | 85 ± 4 |
| Glu-6-Ptase | Bud | .84 ± .13 | .44 ± .05(0.5) | .88 ± .32(1.0) | .70 ± .09(0.8) | 4.20 ± .46 | 8.45 ± 2.31 | 6.69 ± .90 | 68 ± 9 |
| | Epi | .75 ± .21 | 1.29 ± .31(1.7) | — | — | 7.16 ± 1.71 | — | — | 84 ± 5 |
| $(Na^{30}+K^+)$ATPase | Bud | .24 ± .04 | .95 ± .37(4.0) | 2.75 ± .98(11.5) | .68 ± .20(2.8) | 6.57 ± 2.57 | 19.1 ± 1.52 | 3.38 ± 2.91 | 81 ± 4 |
| | Epi | .22 ± .10 | 1.46 ± .11(6.6) | — | — | 6.89 ± .55 | — | — | 89 ± 3 |
| $(Mg^{++})$ATPase | Bud | .92 ± .10 | 14.30 ± 1.42(15.5) | 40.72 ± 15.40(44.3) | 12.85 ± 2.03(14.0) | 8.87 ± .88 | 25.21 ± 5.96 | 7.95 ± 1.26 | 75 ± 3 |
| | Epi | .12 ± .37 | 3.54 ± .67(29.5) | — | — | 2.60 ± .49 | — | — | 84 ± 6 |
| Alkaline Ptase | Bud | .14 ± .04 | .61 ± .09(4.4) | 3.29 ± 1.24(23.5) | .38 ± .11(2.7) | 3.77 ± .59 | 20.01 ± 4.83 | 5.02 ± 1.69 | 84 ± 5 |
| | Epi | .20 ± .08 | 1.71 ± .14(8.6) | — | — | 8.61 ± .69 | — | — | 74 ± 3 |
| 5'Nucleotidase | Bud | .85 ± .12 | 2.49 ± .37(2.9) | 2.09 ± .98(2.5) | 3.06 ± .08(3.6) | 9.61 ± 1.82 | 7.80 ± 2.35 | 11.45 ± .31 | 67 ± 5 |
| | Epi | 1.10 ± .34 | 28.85 ± 5.11(26.2) | — | — | 12.00 ± 2.13 | — | — | 68 ± 3 |
| Esterase | Bud | .23 ± .05 | 2.46 ± 1.18(10.7) | 2.37 ± 1.15(10.3) | 1.96 ± .44(8.5) | 8.97 ± 4.28 | 8.60 ± 4.31 | 7.14 ± 1.63 | 101 ± 10 |
| | Epi | .14 ± .09 | 2.59 ± .32(18.5) | — | — | 7.76 ± .95 | — | — | 98 ± 4 |

[1] Specific enzyme activity is expressed as μmoles of substrate altered per hour per mg protein.
[2] For each cellular fraction % recovery is relative to respective $P_2$, $P_3$ and $P_4$ fractions and is based on the recovery from the initial filtrate as 100%.
[3] Taste bud and epithelial membrane fractions $P_{2(D)}$, $P_{3(D)}$ and $P_{4(D)}$ were obtained from differential and gradient centrifugation. See Methods.
[4] Bud- Taste Buds; Epi- Epithelial tissue.
[5] M ± 1SEM of three determinations from each of three separate preparations.
[6] ( ) - Relative specific activity is specific activity of the membrane fraction relative to the specific activity of the filtrate.
[7] No enzymatic activity found in $P_{3(D)}$ or $P_{4(D)}$ epithelial tissue subfraction.

TABLE V

PROTEIN RECOVERY IN BOVINE TASTE BUD AND FRACTIONS AND SUBFRACTIONS

|  | Taste Bud | | Epithelium | |
|---|---|---|---|---|
|  | Recovery (%) | Protein (mg) | Recovery (%) | Protein (mg) |
| Sample | 100 | 720.0[1] | 100 | 720 |
| Filtrate | 8.18 | 58.9[2] | 3.61 | 26.0 |
| Membrane Enriched Subfractions[3] | .33 | 2.4 | .04 | .3 |

[1]Based upon samples of taste bud papillae and epithelial tissue from forty cow tongues, each with a wet weight of 6 gm and estimated to contain 12% protein.
[2]Duplicate determinations from two separate preparations.
[3]Sum of bovine taste bud [$P_{2,3,4(B)}$] and epithelial [$P_{2,4(B)}$] subfractions obtained by differential and gradient centrifugation. See Methods.

TABLE VI

Chemical Analysis of Comparable Bovine Taste Bud and Epitelial Tissue Subfractions $P_{2(B)}$ and $P_{4(B)}$

|  |  | Subfractions[1] | |
|---|---|---|---|
|  |  | $P_{2(B)}$ | $P_{4(B)}$ |
| Phospholipid phosphorus | Bud-[2] | 58.2±5.2[3] | 149.3±11.3 |
|  | Epi.- | 18.1±1.3 | 19.9±2.1 |
| Cholesterol | Bud- | 26.4±3.2 | 74.9±5.2 |
|  | Epi.- | 11.1±1.2 | 19.4±2.5 |
| Total hexose | Bud- | 12.8±2.1 | 11.1±0.5 |
|  | Epi. | 14.7±4.8 | 13.2±1.3 |
| Hexosamine | Bud- | 28.1±2.3 | 29.5±1.5 |
|  | Epi.- | 5.1±1.1 | 2.6±1.0 |
| Sialic Acid | Bud- | 1.7±0.1 | 1.7±0.3 |
|  | Epi.- | 0.2±0.1 | 0.3±0.1 |
| DNA | Bud- | 13.2±1.1 | 16.6±1.3 |
|  | Epi.- | 1.1±0.1 | 1.2±0.1 |
| RNA | Bud- | 25.0±1.3 | 27.9±3.7 |
|  | Epi.- | 5.5±1.0 | 17.6±4.3 |

[1]Obtained by differential and gradient centrifugation. See Methods.
[2]Bud- Taste bud sample; Epi.- Epithelial sample.
[3]Results are expressed as μg sample/mg protein. Values represent M+1 SEM of two determinations from three separate preparations.

TABLE VII

Chemical Analysis of Comparable Bovine Taste Bud and Epithelial Tissue Subfractions $P_{2(B)}$ and $P_{4(B)}$

|  |  | Subfractions[1] | |
|---|---|---|---|
|  |  | $P_{2(B)}$ | $P_{4(B)}$ |
| [3]Protein (mg) | Bud-[2] | 0.05 | 0.06 |
|  | Epi.- | 0.03 | 0.03 |
| Lipid (mg) | Bud- | 0.02 | 0.02 |
|  | Epi- | 0.03 | 0.04 |
| Cholesterol (μmole) | Bud- | 0.27 | 0.61 |
|  | Epi.- | 0.14 | 0.17 |
| Phospholipid (μmole) | Bud- | 0.30 | 0.59 |
|  | Epi.- | 0.28 | 0.35 |
| Protein/Lipid (W/W) | Bud- | 2.50 | 3.00 |
|  | Epi.- | 1.00 | 0.75 |
| Cholesterol/Phospholipid (μmole/μmole) | Bud- | 0.90 | 1.04 |
|  | Epi.- | 0.50 | 0.49 |

[1]Obtained by differential and gradient centrifugation. See Methods.
[2]Bud- Taste bud sample; Epi.- Epithelial sample.
[3]Results represent the mean of two determinations from two separate preparations.

The foregoing describes a total fractionation of material from taste buds the results of which are compared with those of control tissue treated in the same manner. This comparison establishes, on the basis of morphological, densitometric, enzymatic and chemical studies, that $B$ subfractions isolated from taste buds were membrane enriched whereas those isolated from epithelial tissue were much less so. Further, within the $B$ subfractions isolated from taste buds $P_{4(B)}$ appeared, by the above criteria, to contain the greatest membrane enrichment of any of the taste bud subfractions studied. Although there was substantial enzymatic activity in $D$ subfractions from both taste buds and epithelial tissue these subfractions were denser than those commonly associated with purified membrane fragments and morphologically contained relatively few membrane fragments with respect to the large amounts of other cellular organelles present.

Other investigators in their isolation of membrane fractions from various tissues have noted densities of isolates similar to those which we observed in the B subfractions. Quantitative increases in specific activity of alkaline phosphatase in purified membranes with respect to the starting homogenate similar to that which was obtained in the $P_{4(B)}$ taste bud subfraction were obtained by other investigators working with membranes from kidney brush border and intestinal villi. The ratio of cholesterol/phospholipid for $P_{2,4(B)}$ taste bud subfractions (Table VII) agrees with values obtained by others for plasma membrane fractions of erythrocytes, villi of intestinal epithelium, myelin and Hela cell preparations. The ratios of protein/lipid for taste bud subfractions $P_{2,4(B)}$ are similar to those of plasma membrane fractions obtained from villi of intestinal epithelium [(range of ratios- 1.5–4.0)]. However, the ratios of cholesterol/phospholipid and protein/lipid in epithelial subfractions $P_{2,4(B)}$ are not consistent with values obtained following isolation and purification of cellular membranes from several tissues; they were less than ½ previously reported values for such membranes. Consideration of these results and comparisons indicate that membranes have been enriched in taste bud subfractions $P_{2,3,4(B)}$.

Since contamination of taste bud membrane protein with protein from other sources in the papilla (e.g., glands, epithelium) may occur activities of several enzymes were compared in taste bud subfractions in cored (central mucous glands removed) and uncored (central mucous glands not removed) papillae. Results indicated that taste bud subfractions $P_{2,4(B)}$ isolated from papillae without coring exhibited five-fold and two-fold increases in alkaline phosphatase activity, respectively, over that of similar subfractions isolated from cored papillae. There were no other significant differences in activity of alkaline phosphatase, esterase or other enzymatic activities among other taste bud subfractions isolated from cored or uncored papillae. These results support previous histochemical studies in which high levers of alkaline phosphatase were found in serous and mucous glands of taste bud bearing papillae. These results also indicate the need for careful attention to anatomical details in order to obtain meaningful biochemical information.

Estimates of the percent organelle protein associated with acid phosphatase, succinic cytochrome-c-reductase and glucose-6-phosphatase in taste bud subfractions $P_{2,3,4(B)}$ were made using the methods of DeDuve, et al. (1955) Biochemical J. 60, 604–617, as follows: specific activity of a given marker enzyme in each taste bud fraction (Table III) was divided by the specific activity of the marker enzyme in the initial filtrate. The resulting relative specific activity was then multiplied by the percent of that organelle protein in the initial filtrate. The latter values were estimates derived from the fractionation data in Table II by subtracting protein contaminants and adding organelle protein distributed in other fractions to the values for $P_2$ fractions (which were assumed to contain mainly nuclear fractions), for $P_3$ fractions (which were assumed to contain primarily mitochondrial and lysosomal fractions) and for $P_4$ fractions (which were assumed to contain mainly microsomal fractions). Since $P_3$ fractions may contain both mitochondrial and lysosomal associated enzymes, the percent of organelle protein associated with succinic cytochrome-c-reductase and acid phosphatase in taste bud membrane fractions was calculated over a similar estimated initial filtrate percent organelle protein; these values were between 26% and 30% for acid phosphatase and succinic cytochrome-c-reductase and was 35% for glucose-6-phosphatase. The percent organelle associated enzyme protein present in the taste bud subfractions $P_{2,3,4(B)}$ for acid phosphatase activity was calculated to be approximately 2% for each subfraction, for succinic cytochrome-c-reductase activity it was 0.6%, 1.6% and 0.3%, respectively and for glucose-6-phosphatase activity it was 2.1%, 0.2% and 2.5%, respectively.

Since there are no biological or anatomical markers by which specific membranes from taste buds can be identified, it is difficult to obtain specific correlations between the crude filtrate isolated from taste bud bearing circumvallate papillae and membranes obtained and purified from the enriched taste bud subfractions treated on these studies. It was necessary then to rely upon chemical analysis and enzyme markers to identify the various cellular organelles isolated and to assist in the establishment of purity. To reach these ends a consistent attempt was made to obtain the maximal amount of taste bud material with the least damage to and contamination from epithelial and other tissue surrounding the taste buds and to isolate taste bud protein of greatest specificity, sacrificing yield, which was low, for purity.

Other investigators, using light and electron histochemical microscopy, attempted to localize some of the enzymes measured in this study in various portions of taste buds and in non taste bud bearing portions of lingual epithelium from several different species. Localized in the microvilli of taste buds were ATPase, acid phosphatase, sulfhydryl groups, 3' and 5' nucleotidase, esterase and alkaline phosphatase. Localized in smaller amounts in the more apical region of the taste bud was acid phosphatase, sulfhydryl groups, 5' nucleotidase, esterase, alkaline phosphatase and succinic dehydrogenase. In lingual epithelium, in comparison with that found in taste buds, large amounts of acid phosphatase, esterase, succinic dehydrogenase, and visibly smaller amounts of alkaline phosphatase and 5' nucleotidase were found; ATPase was observed only sparsely, the major concentration found in taste buds adjacent to the pore.

The enrichment of alkaline phosphatase and of ATPase shown biochemically in these studies correlates closely with the previous histochemical localization of these enzymes in taste buds and could relate to some functional significance of these enzymes in the taste process. Previous localization of alkaline phosphatase in the peripheral part of the apical portion of taste bud cells suggested to several earlier investigators a role for this enzyme in the taste process. To support this concept functionally, it was demonstrated that 14 phosphate esters were hydrolyzed in taste bud microvilli at the site of alkaline phosphatase localization. Functional studies by others lent support to this concept. Surgical section of taste nerves resulted in decreased taste bud alkaline phosphatase and ATPase activities; however, acid phosphatase, an enzyme normally found in greater concentrations in epithelium than in the taste bud increased in concentration rather than decreased. Cysteine, which decreased taste bud alkaline phosphatase activity histochemically, also decreased taste acuity following its systemic administration in animals; decreased taste acuity was also observed concomitantly with elevated circulating SH levels in man. Zinc is known to be at the active site of alkaline phosphatase. This metal also appears to play an active role in the taste process and has been localized in or near taste buds in rat circumvallate papillae. Depletion of body zinc has produced decreased taste acuity in both man and animals. The histochemical and biochemical localization of $(Na^+ + K^+)$ and $Mg^{++}$ATPase at the apical area of taste buds, in an area similar to that where alkaline phosphatase was found, also implicates these enzymes in the taste process. Recent studies have localized these latter enzymes on the external surface of membranes obtained from cultured cells and have implicated them as "ecto-enzymes". Further speculation about the chemical basis of the preneural events of taste and the roles of these and other enzymes must await functional studies before specific conclusions may be drawn.

III. EVALUATING THE BINDING PROPERTIES OF MATERIALS WITH THE ISOLATED AND PURIFIED TASTE BUD MEMBRANE SUBFRACTIONS

As hypothesized, taste acuity depends upon the formation of a weak tastant-receptor complex at the apical surface of the taste bud. Evaluation of acuity then depends upon the binding properties of the tastant and the membrane enriched subfraction. The following is an evaluation of different sugars chosen as sample tastants to prove the foregoing hypothesis. It will be obvious from the following that this procedure may be utilized to screen any material for taste acuity.

Binding properties of various sugars were compared in purified subfractions of taste buds isolated from bovine circumvallate papillae and, as a control, of non-taste bud bearing epithelium isolated from tissue surrounding these papillae according to the procedures outlined above.

In summary, however, binding of $^{14}C$ sugars was predictably found to be greater in purified subfractions obtained from taste bud than from non-taste bud bearing tissue and was, in general, greater in those taste bud subfractions in which a greater membrane purification was achieved. Binding specificity of the $^{14}C$ labeled sugars sucrose, fructose, glucose, and the synthetic sugar substitutes, (hereinafter SSS), cyclamate and saccharine was measured by competition of each $^{14}C$ sugar or SSS with its unlabeled homologous sugar in $P_{4(R)}$ taste bud subfractions; this binding, as will be described for sucrose, was reversible and temperature dependent. Essentially no competition of the $^{14}C$ labeled sugars sucrose, fructose, glucose, or SSS cyclamate and saccharine by their respective unlabeled homologous sugars or SSS occurred in epithelial tissue $P_{4(B)}$ subfractions; this binding was also not reversible. Epithelial tissue $P_{4(B)}$ subfractions then serve as controls.

Binding specificity was further observed by the competition of $^{14}C$ labeled sucrose, fructose and glucose with each unlabeled sugar for binding sites on $P_{4(B)}$ taste bud subfractions; unlabeled sucrose was found to be more effective in competing with each $^{14}C$ sugar than was unlabeled fructose or glucose. The relatively non-sweet sugar lactose did not compete with $^{14}C$ labeled lactose in $P_{4(B)}$ subfractions from either taste bud or non-taste bud bearing epithelial tissue. Binding of $^{14}C$ sucrose in purified $P_{4(B)}$ bud subfractions was inhibited by increased concentrations of unlabeled sucrose, phospholipase C, neuraminidase, EDTA (ethylenediaminetetraacetic acid), NaCl (salt taste) and urea (bitter taste).

Dissociation constants for sugar binding were low ($\sim 10^{-3}$M) but in a rank order (sucrose > fructose > λ glucose > > saccharine) consistent with preference and electrophysiological responses in cow. The cow is known to be behaviorally indifferent to saccharine and lactose consistent with the data obtained.

The following materials were used in the tastant evaluation according to the process of this invention: $^{14}$C sucrose (394 mCi/mmole), $^{14}$C fructose (121 mCi/mmole) $^{14}$C glucose (183 mCi/mmole) and $^{14}$C lactose (14.9 mCi/mmole) were obtained from New England Nuclear Corporation, Boston, Mass. $^{14}$C cyclamate (1.7 mCi/mmole) and $^{14}$C saccharine (4.6 mCi/mmole) were obtained from Mallinckodt, Inc., St. Louis, Mo. Neuraminidase from *Clostridium perfringens*, Worthington Foods, Inc., Worthington, Ohio, (1 unit/ml; i.e., 1 mmole sialic acid released/min) was purified by ion exchange chromatography and supplied by Dr. G. Ashwell, NIH. Phosphalipase A (209 units/ml; i.e., 1 unit = ΔOD 546/min = 0.110 at pH 8.95) from *Vipera russelli* and phospholipase C from Clostridium perfringens (0.6 units/mg; i.e., 1 unit = 1 μmole Pi released/min) were obtained from Sigma Chemical Co., St. Louis, Mo., purified by ion exchange chromatography and supplied by Dr. G. Ashwell, NIH. Microcentrifuge and plastic micro test tubes (0.4 ml capacity) were obtained from the Brinkman Instruments, Inc., Westbury, N.Y.

The following procedure was utilized in tastant evaluation according to the process of this invention: Protein concentrations were determined by the methods of Lowry et al., (1951) J. Biol. Chem. 193, 265–275, with crystalline bovine serum albumin (Sigma) as standard. Taste bud and epithelial tissues from six different preparations of bovine tongues were isolated and several pellets or tissue fractions ($P_2, P_3, P_4$) and subfractions ($P_{2,3,4(B)}$, $P_{2,3,4(D)}$) were obtained by differential and sucrose gradient centrifugation as described above. According to density, physical appearance as determined by using electron microscopic morphology enzymatic activity and chemical analysis, B subfractions from taste buds and epithelial tissues achieved the greatest membrane purification compared with other subfractions. Among the taste bud B subfractions, $P_{4(B)}$ was morphologically more homogeneous with respect to membranes than $P_{3(B)}$ whereas $P_{2(B)}$ was the least homogeneous of all. Epithelial tissue B subfractions contained mainly fibrous tissue and few differences were found in morphology, density, enzymatic activity or chemical analysis between $P_{2(B)}$ or $P_{4(B)}$ subfractions. Taste bud and epithelial tissue D subfractions contained relatively few membrane fragments compared to the large amount of other cellular organelles present and therefore were not included in these studies. Therefore, for the binding studies filtrates and enriched B subfractions from taste bud and epithelial tissue, containing 3–5 μg protein, were used.

Each filtrate and subfraction was washed three times with calcium free, 0.2 M Krebs-Ringer bicarbonate (KRB) pH 7.4, suspended in the same buffer in a final volume of 2 ml and frozen in liquid nitrogen. No detectable change in binding characteristics from suspensions of taste bud or epithelial tissue fractions was observed after storage at −80° for as long as two months.

Experiments using material from taste buds were carried out with corresponding non-taste bud bearing material from epithelium, in parallel, except in time and temperature, and binding inhibition studies in which only taste bud material was used. Each experimental point noted in the Figures to be hereinafter explained was determined in duplicate or triplicate in each of two or three preparations of tissue suspensions; and mean values were reported.

All binding studies were carried out in plastic micro test tubes in a constant temperature shaking bath. For these studies KRB, suspensions of the initial filtrates, subfractions and $^{14}$C labeled and/or unlabeled sugars were incubated in a final volume of 100 μl. After incubation the tubes were placed in an ice bath, centrifuged, the supernatant aspirated and 10 μl KRB layered on top of the pellet.

The KRB was then aspirated, the top of the test tube cut off with a razor blade just above the bellet, placed into 10 ml Aquasol (New England Nuclear Corp., Boston, Mass.) and the radioactivity determined in a liquid scintillation spectrophotometer. Controls, without filtrates or subfractions, were also included. These controls represent background radioactivity composed mainly of $^{14}$C sugars bound to the walls of the plastic test tubes. This background radioactivity was always found to be less than 1% of the lowest level obtained in any study with added tissue fractions. Calculations of $^{14}$C sugar binding also included a correction for non-specific binding (i.e., $^{14}$C sugar binding not inhibited by an excess of the unlabeled homologous sugar, which occurred when tissue suspensions were used. This value (40%) was the mean calculated from the results of 56 duplicate experiments.

Filtrate and B Subfraction Binding

Suspensions from filtrates and from B subfractions from taste buds [$P_{2,3,4(B)}$] and from non-taste bud bearing epithelial tissue [$P_{2,4(B)}$, no $P_{3(B)}$ subfraction was obtained] from two tissue preparations were used in duplicate. $^{14}$C glucose (200 μM), fructose (400 μM), sucrose (26 μM), and KRB was added, the mixture incubated for 30 min at 30° C. The tubes were then placed in an ice bath for 3 minutes, and then centrifuged at 15,000 rpm for 6 min. The sugar bound was expressed as the total radioactivity bound to the pellets with $^{14}$C sugars added minus the background radioactivity.

Time and Terperature Effects $^{14}$C sucrose (26 μM), KRB and suspensions from one preparation of taste bud subfraction $P_{4(B)}$ were incubated at 0° C. and 30° C. for 10 to 50 min. Following incubation test tubes were assayed as before. In all subsequent studies incubations were carried out at 30° C. for 30 min except where specifically noted.

Displacement $^{14}$C sucrose (26 μM), KRB and suspensions from $P_{4(B)}$ subfractions were initially incubated for 30 min at 30° C. Unlabeled sucrose (0.01–1 mM) was added to give a final volume of 100 μl, the solutions incubated for an additional 20 min, and assayed as before. The amount of sucrose bound was expressed as the total radioactivity bound to the membrane pellet after addition of unlabeled sucrose minus the background and non-specific activity.

Specific Binding $^{14}$C labeled glucose (200 μM), fructose (400 μM), lactose (670 μM), cyclamate (5.4 mM), saccharine (1.6 mM), each respective unlabeled sugar (0.1 mM–1M), or SSS KRB and suspensions from $P_{4(B)}$ subfractions were incubated together. $^{14}$C labeled and unlabeled glucose, fructose, and sucrose (0.01-100 mM), KRB and suspensions from $P_{4(B)}$ subfractions were also incubated such that each $^{14}C$ sugar or SSS was incubated with every other unlabeled sugar. Specific binding, calculated as before, was defined as the amount of $^{14}C$ labeled sugar or SSS bound after addition of unlabeled sugar or SSS minus background and non-specific activity.

Binding Inhbition

Suspensions of taste bud subfraction $P_{4(B)}$, KRB, and graded concentrations of various substances including neuraminidase (4-27 μg), phospholipase A (20-60 μg), phospholipase C (5-30 μg), EDTA (5-20 mM), NaCl (0.5-3 M) and urea (1-5 M) were incubated in triplicate. EDTA (5 mM) was also used alone or with a graded series of concentrations of $Zn^{++}$ as $ZnCl_2$ (1-20 mM) in the same manner, in duplicate, with taste bud $P_{4(B)}$ suspensions. These mixtures were initially incubated for 20 min at 30° C.; 26 μM $^{14}C$ sucrose were then added to each solution to obtain the final 100 μl volume and incubated for an additional 30 min. Control tubes, without any of the above added substances, were treated in triplicate in the same manner.

RESULTS

Binding of various sugars to taste bud and epithelial tissue B subfractions are shown in Table VIII. For taste bud subfraction $P_{4(B)}$, compared to the initial filtrate, there was a respective 9,18 and 24 fold increase in sugar binding for $^{14}C$ labeled glucose, fructose and sucrose; for $P_{3(B)}$, there was a comparable 10,8 and 7 fold increase; for $P_{2(B)}$, there was an approximate 3 fold increase for each sugar. However, for epithelial B subfractions there was no increase in sugar binding for any sugar used.

Temperature dependence of binding of $^{14}C$ sucrose to taste bud subfraction $P_{4(B)}$ is shown in FIG. 3. There was an approximate four fold increase of sucrose binding activity following the increase in incubation temperature from 0° C. to 30° C. A plateau was reached after about 25 min at 30° C. Binding of sucrose was linearly dependent upon the concentration of protein from taste bud subfraction $P_{4(B)}$ up to 2 mg/ml. (FIG. 4).

TABLE VII
BINDING OF $^{14}C$ SUGARS TO TASTE BUD AND EPITHELIAL FILTRATES FILTRATES AND B SUBFRACTIONS

| | | Sugar | | |
|---|---|---|---|---|
| Fraction | Source | $^{14}C$ Glucose | $^{14}C$ Fructose | $^{14}C$ Sucrose |
| | | (× 10-4cpm/mg protein) | | |
| Filtrate | Bud[1] | 3.7[2] | 15.3 | 3.6 |
| | Epi | 2.2 | 8.8 | 3.3 |
| $P_{2(B)}$[3] | Bud | 12.0 (3.2)[4] | 56.9 (3.7) | 11.3 (3.1) |
| | Epi | 2.9 (1.3) | 9.5 (1.1) | 3.7 (1.1) |
| $P_{3(B)}$[5] | Bud | 36.0 (9.7) | 130.0 (8.5) | 25.5 (7.0) |
| $P_{4(B)}$ | Bud | 34.8 (9.4) | 272.5 (17.8) | 86.8 (23.8) |
| | Epi | 1.7 (0.8) | 7.8 (0.9) | 1.8 (0.5) |

[1] Bud- Taste bud; Epi- Epithelial tissue.
[2] Mean of duplicate determinations from each of two tissue preparations [Cf methods (15)].
[3] Subfractions obtained by differential sucrose gradient centrifugations [Cf methods (15)].
[4] ( ): Relative enrichment of sugar binding compared to the initial filtrate.
[5] No $P_{3(B)}$ subfraction was obtained from epithelial tissue fraction $P_3$.

TABLE IX
BINDING INHIBITION[1] of $^{14}C$ LABELED GLUCOSE, FRUCTOSE, AND SUCROSE BY UNLABELLED SUGARS FROM TASTE BUD $P_{4(B)}$ SUBFRACTIONS

| Unlabelled Sugars | Inhibition (%) | | |
|---|---|---|---|
| | $^{14}C$ Glucose | $^{14}C$ Fructose | $^{14}C$ Sucrose |
| Glucose | 70-80 | 14-20 | 14-20 |
| Fructose | 36-40 | 70-80 | 14-20 |
| Sucrose | 60-65 | 50-60 | 70-80 |

[1] Binding inhibition represents $B/B_o$ of the sugar binding to taste bud subfraction $P_{4(B)}$ in the presence of maximal concentrations of homologous and heterologous unlabelled sugars (FIG. 6).
[2] Range of values.

TABLE X
BINDING PARAMETERS OF SUGARS TO TASTE BUD $P_{4(B)}$ SUBFRACTIONS

| Sugar | Kd[1] | $q^2$ | Relative Binding Inhibition[3] |
|---|---|---|---|
| | mM | mM/mg protein | % |
| SUCROSE | 1.1 ± 0.4 | 51 ± 8 | 100 |
| Fructose | | | 59 |
| Glucose | | | 32 |
| FRUCTOSE | 1.8 ± 0.9 | 10.5 ± 1.2 | 100 |
| Sucrose | | | —[4] |
| Glucose | | | 51 |
| GLUCOSE | 3.4 ± 1.1 | 2.5 ± 0.5 | 100 |
| Sucrose | | | —[4] |
| Fructose | | | —[4] |
| CYCLAMATE | | | |
| $K_1$ | 11.7 ± 2.4 | 4.0 ± 0.9 | |
| $K_2$ | 32.6 ± 3.9 | 6.6 ± 1.4 | |
| SACCHARINE | | | |
| $K_1$ | 18.3 ± 3.9 | 2.7 ± 1.0 | |
| $K_2$ | 66.2 ± 6.8 | 6.4 ± 0.4 | |

[1] Dissociation constant. Values represent mean ± 1 SEM of duplicate determinations from three tissue preparations.
[2] Concentration of sugar or SSS bound per mg subfraction protein.
[3] Maximal binding inhibition after incubation of each underlined capitalized sugar or SSS as the $^{14}C$ sugar or SSS, with each unlabelled sugar or SSS. Incubation of the $^{14}C$ sugar with the homologous unlabeled sugar was arbitrarily set at 100 for comparison.
[4] No displacement was measured.

Displacement of $^{14}C$ sucrose initially bound to taste bud subfractions $P_{4(B)}$ was observed after addition of unlabeled sucrose (FIG. 5). The maximum displacement was about 80% of the $^{14}C$ sucrose initially bound. Binding of $^{14}C$ sucrose to epithelial $P_{4(B)}$ subfractions could not be reversed by addition of excess unlabeled sucrose. Binding of $^{14}C$ sucrose to taste bud $P_{4(B)}$ subfractions with subsequent displacement with unlabeled sucrose over time illustrates that displacement is rapid compared to the slower initial binding, that displacement follows first order kinetics and that $t_{\frac{1}{2}}$ is approximately two minutes (FIG. 6).

Specific binding of $^{14}C$ labeled sucrose, fructose, glucose, cyclamate and saccharine to taste bud $P_{4(B)}$ subfractions occurred as shown by the competition of each $^{14}C$ sugar or SSS with its homologous unlabeled sugar or SSS (FIG. 7). No specific binding of any $^{14}C$ sugar or SSS for epithelial $P_{4(B)}$ subfractions occurred, shown by the inability of each unlabeled sugar or SSS to compete with its homologous $^{14}C$ sugar or SSS (FIG. 7). By these criteria lactose did not bind specifically to either taste bud or epithelial tissue $P_{4(B)}$ subfractions.

Incubation of taste bud $P_{4(B)}$ subfractions with $^{14}C$ labeled sucrose, fructose or glucose and graded concentrations of unlabeled glucose resulted in little competition with the $^{14}C$ sucrose or fructose (FIG. 8) but marked compeition with the $^{14}C$ glucose as previously shown (FIG. 7); eighty percent of the $^{14}C$ glucose binding was inhibited by unlabeled glucose (Table IX). Incubation of $^{14}C$ glucose, fructose, and sucrose with graded concentrations of unlabeled sucrose resulted in competition with each $^{14}C$ sugar (FIG. 8); addition of unlabeled sucrose resulted in the greatest inhibition of the $^{14}C$ sucrose, the final inhibition being about 80% (Table IX). Unlabeled sucrose was more effective in competing with glucose than fructose at all concentrations of sugars added although the differential effect was more clearly observed at lower concentrations. Incubation of $^{14}C$ labeled sucrose, glucose and fructose with graded concentrations of unlabeled fructose resulted in inhibition of glucose binding but little inhibition of sucrose binding. Maximal inhibition of $^{14}C$ fructose binding with unlabeled fructose was about 80% (Table IX) (FIG. 8).

Characteristics of binding of each sugar or SSS to $P_{4(B)}$ taste bud and epithelial tissue subfractions is shown in FIG. 9. Linear Scatchard plots [See (1949) Ann. N.Y. Acad. Sci. 51,660] for the steady state binding of $^{14}C$ labeled sucrose, fructose, and glucose, inhibited by their homologous unlabeled sugars, calculated from their binding curves (FIG. 7), suggest the presence of at least a single class of saturable binding sites. For sucrose, a possible secondary class of binding sites may be suggested but the low level of activity associated with the non-linear portion of the plot makes this interpretation difficult. A non-linear Schatchard plot was calculated for binding of $^{14}C$ labeled cyclamate and saccharine when inhibited by their homologous unlabeled SSS. This suggested the presence of at least two classes of binding sites, a primary class in the linear portion of the plots and possibly a secondary class, as suggested by the non-linear portion of the plots. No specific binding of any sugar was observed to epithelial tissue $P_{4(B)}$ subfractions.

Dissociation constants for sucrose, fructose, glucose, cyclamate and saccharine were calculated by obtaining the reciprocal slope from each of the Scatchard plots in FIG. 9 (Table X). Sucrose had the lowest dissociation constant of any sugar or SSS studied. Expressed as sugar binding capacity per mg subfraction protein, the amount of fructose bound to taste bud $P_{4(B)}$ subfractions was greater than that of any substance studied.

Binding of $^{14}C$ sucrose to taste bud $P_{4(B)}$ subfractions was inhibited significantly by neuraminidase, phospholipase C, EDTA, NaCl and urea, but only slightly by phospholipase A (FIG. 10). At the highest concentrations used sucrose binding was inhibited by approximately 40% with neuraminidase (27 μg/ml) or phospholipase C (30 μg/ml), 50% with NaCl (3M) and 30% with urea (5M). The inhibitory effects of 5 mM EDTA (about 40%, FIG. 10) were progressively reversed by addition of relatively high concentrations of $ZnCl_2$ (FIG. 11); after addition of 20 mM $Zn^{++}$, sucrose binding activity was restored to about 85% of the initial activity measured in the absence of EDTA.

The foregoing demonstrates that sugars or SSS bind to various biological tissues. However, it also demonstrates that sugar or SSS binding to tissue fractions obtained from taste buds is greater than to tissue fractions obtained from lingual epithelium. These studies also indicate that sugar or SSS binding to taste buds fractions increases as these fractions are purified with respect to their membrane content. Sugar binding of each sugar to each taste bud subfraction, regardless of degree of membrane purification, was greater than that for each correspondingly purified epithelial tissue subfraction.

This also demonstrates, for the first time, that sugars or SSS bind specifically to purified taste bud subfractions but not to non-taste bud bearing epithelial tissue in which subfractions were obtained and purified in the same manner.

Binding is temperature dependent; it is also concentration dependent and reversible if carried out with purified taste bud subfractions. It is not reversible if carried out with purified non-taste bud bearing epithelial subfractions.

Dissociation constants for all sugars or SSS studied were high, of the order of 1 mM. Whereas these constants are significantly greater than those usually considered in the binding of metabolic regulators to their receptors the taste system may, of necessity, represent a system with different physiological requirements. In taste, tight binding could result in persistence of the tastant-receptor complex and produce taste confusions. It appears to be the nature of the tastant-receptor complex to take the form of a weak binding so that new taste information may be sequentially processed by the taste receptors on the tongue.

As shown in FIG. 8 sucrose, which consists of glucose and fructose, competed with both glucose and fructose. On the other hand, glucose did not compete with either fructose or sucrose whereas fructose competed with glucose but did not sucrose. The results indicate that there may be specific sites on the taste bud to which sucrose, fructose and glucose are bound. These results would also suggest that sucrose occupies the sites for glucose and fructose, but the latter do not bind to the sucrose site.

Various substances inhibit sugar or SSS binding to taste bud subfractions. Inhibition of sucrose binding by EDTA suggests that divalent cations may be important in the binding process and previous physiological and chemical data have suggested that a metal-thiol moeity may play a role at the taste receptor. Zinc has been shown to be present in or near the taste bud. Topical lingual application of cadmium has been shown to inhibit electrophysiologically measured responses to several tastants applied to the lingual surface. In the present studies, addition of $Zn^{++}$, albeit in high concentrations, reversed the inhibitory effects of EDTA without detrimentally altering sugar binding.

Inhibition of sucrose binding by neuraminidase suggests that sialic acid residues may be important in the binding process and these residues have been previously demonstrated by chemical analysis in these purified taste bud subfractions. These results suggest that glycoproteins may play some role in the taste process, a concept previously suggested from the presumed binding of a plant glycoprotein to the taste bud thereby changing the taste of all sour substances to sweet.

Inhibition of sucrose binding by phospholipase C suggest that phospholipids are important in the binding process and this enzyme also have been previously demonstrated by chemical analysis in these purified taste bud subfractions. Inhibition by NaCl may be the result of ionic effects on taste receptor sites. However, the effects of NaCl in taste bud subfractions differ from its effects on insulin receptors in liver and fat cells where its addition, at concentrations used here, enhanced the binding of insulin.

The rank order of the sugar or SSS binding affinity is in parallel with bovine preference and/or electrophysiological responses to these sugars or SSS [sucrose > fructose > glucose >> saccharine]. On the basis of electrophysiological recordings from bovine glossopharyngeal nerve (the nerve supplying the taste buds used) responses to sucrose occurred at concentrations approximately one-half that of fructose and, one-half that of glucose. Behavioral responses to sugar solutions suggest that cows often prefer sucrose more consistently than fructose. On the basis of electrophysiological and behavioral data bovine response to saccharine were significantly less than to sucrose, fructose or glucose. This is, of course, significantly different from man, in whom saccharine is considered quantitatively sweeter than any of the other natural sugars. Lactose has been reported to be the least acceptable sugar by the calf producing either behavioral indifference or rejection. Cyclamate also appears to produce behavioral indifference on the part of the calf.

On a behavioral basis, bovine discrimination thresholds for sucrose were 0.03 M, for fructose, 0.06 M. These responses, which may be considered recognition thresholds, are approximately 10 times higher than the dissociation constants calculated in this study (Table X). In man, except for saccharine and cyclamate, the rank order of binding affinity of the sugars or SSS used in this study is parallel with known sweetness estimates [sucrose > fructose > glucose]; lactose, which did not bind specifically to bovine taste bud subfractions has very little, if any, sweet taste. Recognition thresholds for sucrose, fructose and glucose in man are between 0.01–0.03 M, roughly similar to the range reported for cow and also approximately 10 times higher than the dissociation constants calculated in these studies ($10^{-3}$M). However, detection thresholds for sucrose in normal man have been reported as low as $5 \times 10^{-3}$M similar to the binding affinities noted herein for the cow.

The foregoing demonstrates that biochemical information about sugar binding or taste acuity for any tastant may be obtained in a systematic manner using the screen process of this invention.

I claim:

1. A process for preparing a medium for evaluating tastants or materials which influence taste, said medium consisting of taste receptor enriched membrane, comprising the steps of:

selecting a plurality of papillae, coring each papillae to remove the central mucous gland, and surgically excising each papillae to separate the taste bud bearing material from surrounding basal serous glands and tissue;

extracting taste receptor materials substantially from the apical portion of said taste buds in said taste bud bearing material with only minimal damage to tissue adjacent said bud by causing said buds to swell and open and subsequently to lose their cellular contents; and isolating and purifying a taste receptor enriched membrane medium from said material, said medium containing substantially no non-receptor containing contaminants capable of binding tastants and other materials by subjecting said materials to differential centrifugation followed by sucrose density gradient centrifugation thereof.

2. The process of claim 1 further comprising isolating and purifying an enriched membrane medium from the epithelial tissue immediately surrounding said taste bud for use as a control against said receptor medium in evaluating tastants or other materials.

3. The process of claim 1 wherein said taste buds are opened by swelling and subsequent application of pressure before removing receptor material therefrom.

4. The process of claim 3 wherein said buds are swelled by exposing said excised papillae to a hypotonic medium.

5. The process of claim 4 wherein after said buds are exposed to a hypotonic medium, said buds are subjected to sufficient pressure to open said buds for removal of receptor materials therein.

6. The process of claim 5 wherein said buds are pressurized in a nitrogen bomb to a pressure of about 900 psi.

7. The process of claim 5 wherein the steps of extracting receptor materials further comprises subjecting said opened buds to a gentle, selective homogenization of a predetermined period of time until receptor material is separated from said buds.

8. The process of claim 7 wherein said homogenization step comprises admixing said buds with a predetermined quantity of an unbuffered sucrose, $CaCl_2$ solution in a precooled glass homogenizer, and subjecting said mixture to about 15 complete strokes of a teflon pestle driven at a speed of about 1,000 rpms.

9. The process of claim 8 further comprising filtering said homogenized mixture and collecting the filtrate for isolating said receptor containing material therein.

10. The process of claim 9 wherein said step of isolating and purifying said medium comprises: differentially centrigugating said filtrate at about 1,000 xg for about 10 minutes; separating the supernatant; resuspending the precipitant in an unbuffered solution of sucrose and $CaCl_2$; centrifuging a second time at 1,000 xg for 10 minutes; repeating the procedure of centrifugation a third and fourth time at about 33,000 xg for about 8 minutes each; combining the supernatants and centrifugating again at 80,000 xg for 100 minutes; collecting a purified receptor membrane containing precipitant as an enriched fraction.

11. The process of claim 10 further comprising purifying a receptor membrane enriched fraction by sucrose gradient centrifugation of said differentially centrifuged fraction comprising: suspending said receptor membrane containing precipitant in a small quantity of said unbuffered sucrose-$CaCl_2$ solution and laying a predetermined quantity of a 35% sucrose solution thereover, followed by a final layer of said unbuffered sucrose-$CaCl_2$ solution; centrifuging said combination at about 75,000 xg for about 16 hours to separate said membrane enriched subfraction from said combination.

* * * * *